(12) United States Patent
Tanaami et al.

(10) Patent No.: US 7,854,897 B2
(45) Date of Patent: Dec. 21, 2010

(54) CHEMICAL REACTION CARTRIDGE, ITS FABRICATION METHOD, AND A CHEMICAL REACTION CARTRIDGE DRIVE SYSTEM

(75) Inventors: Takeo Tanaami, Musashino (JP); Hisao Katakura, Musashino (JP); Saya Satou, Musashino (JP); Naoki Seki, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 1240 days.

(21) Appl. No.: 10/833,158

(22) Filed: Apr. 28, 2004

(65) Prior Publication Data

US 2004/0254559 A1    Dec. 16, 2004

(30) Foreign Application Priority Data

| May 12, 2003 | (JP) | 2003-133564 |
| Jun. 16, 2003 | (JP) | 2003-170453 |
| Jul. 2, 2003 | (JP) | 2003-270261 |
| Jul. 4, 2003 | (JP) | 2003-270916 |
| Jul. 4, 2003 | (JP) | 2003-270917 |

(51) Int. Cl.
  *B01L 3/00* (2006.01)
(52) U.S. Cl. .................. 422/102; 422/100; 422/103
(58) Field of Classification Search ................ 422/102, 422/58, 60, 44, 46, 48, 103, 100
See application file for complete search history.

(56) References Cited

U.S. PATENT DOCUMENTS 3,036,894 A    5/1962    Forestiere
4,007,010 A    2/1977    Woodbridge, III
4,065,263 A  * 12/1977    Woodbridge, III ........... 422/57
4,525,374 A  *  6/1985    Vaillancourt ................. 427/2.3
4,708,931 A   11/1987    Christian
5,422,271 A    6/1995    Chen et al.
5,863,502 A    1/1999    Southgate et al.
6,068,751 A  *  5/2000    Neukermans ............... 204/601
6,426,230 B1   7/2002    Feistel (Continued)

FOREIGN PATENT DOCUMENTS

CN    2470820 Y    1/2002

(Continued)

OTHER PUBLICATIONS

Office Action of German Patent and Trademark Office dated Aug. 31, 2007, issued in corresponding German Patent Application Serial No. 102004023217.2-43.

(Continued)

*Primary Examiner*—Natalia Levkovich
(74) *Attorney, Agent, or Firm*—Westerman, Hattori, Daniels & Adrian, LLP

(57) ABSTRACT

The present invention describes a disposable chemical reaction cartridge comprising a container formed of a rigid substrate and an elastic body, wherein two or more chambers are linked or configured to be linked through flow paths, and wherein the flow paths, the chambers or both, can be partially closed by applying an external force to the elastic body from outside of the container, to move or block fluids in the flow paths or chambers. The cartridge has a structure protected against viruses or dangerous drugs and facilitates foolproof implementation of prescribed protocols for the samples to be tested.

34 Claims, 31 Drawing Sheets

U.S. PATENT DOCUMENTS

| | | |
|---|---|---|
| 7,201,881 B2 | 4/2007 | Cox et al. |
| 2004/0137607 A1 | 7/2004 | Tanaami et al. |
| 2004/0151629 A1 | 8/2004 | Pease et al. |
| 2004/0254559 A1 | 12/2004 | Tanaami et al. |
| 2005/0244308 A1 | 11/2005 | Tanaami et al. |
| 2007/0014698 A1 | 1/2007 | Tanaami |

FOREIGN PATENT DOCUMENTS

| | | |
|---|---|---|
| CN | 1390303 A | 1/2003 |
| CN | 1390606 A | 1/2003 |
| DE | 4341862 A1 | 6/1994 |
| DE | 69213910 T2 | 4/1997 |
| DE | 69305046 T2 | 4/1997 |
| DE | 10001116 A1 | 7/2001 |
| DE | 10041853 C1 | 2/2002 |
| DE | 10222478 A1 | 12/2003 |
| DE | 102004023217 A1 | 12/2004 |
| EP | 0 381 501 A2 | 8/1990 |
| EP | 0803288 A2 | 10/1997 |
| EP | 1508368 A1 | 2/2005 |
| GB | 2 295 892 A | 6/1996 |
| JP | 03-007571 A | 1/1991 |
| JP | 05-261270 A | 10/1993 |
| JP | 8160031 A | 6/1996 |
| JP | 2001-070784 A | 3/2001 |
| JP | 3166144 | 5/2001 |
| JP | 2002-022753 A | 1/2002 |
| JP | 2002-282682 A | 10/2002 |
| JP | 2002-365299 | 12/2002 |
| JP | 2003-004752 A | 1/2003 |
| JP | 2003-139660 A | 5/2003 |
| JP | 2005-037368 A | 2/2005 |
| WO | 97/27324 A1 | 7/1997 |
| WO | 98/40466 A1 | 9/1998 |
| WO | 01/07892 A1 | 2/2001 |
| WO | 02/100543 A1 | 12/2002 |
| WO | 03/099428 A1 | 12/2003 |
| WO | 03/099988 A1 | 12/2003 |
| WO | 2004/011147 A1 | 2/2004 |

OTHER PUBLICATIONS

Office Action of German Patent and Trademark Office dated Aug. 31, 2007, issued in corresponding German Patent Application Serial No. 102004023217.2-43.

* cited by examiner

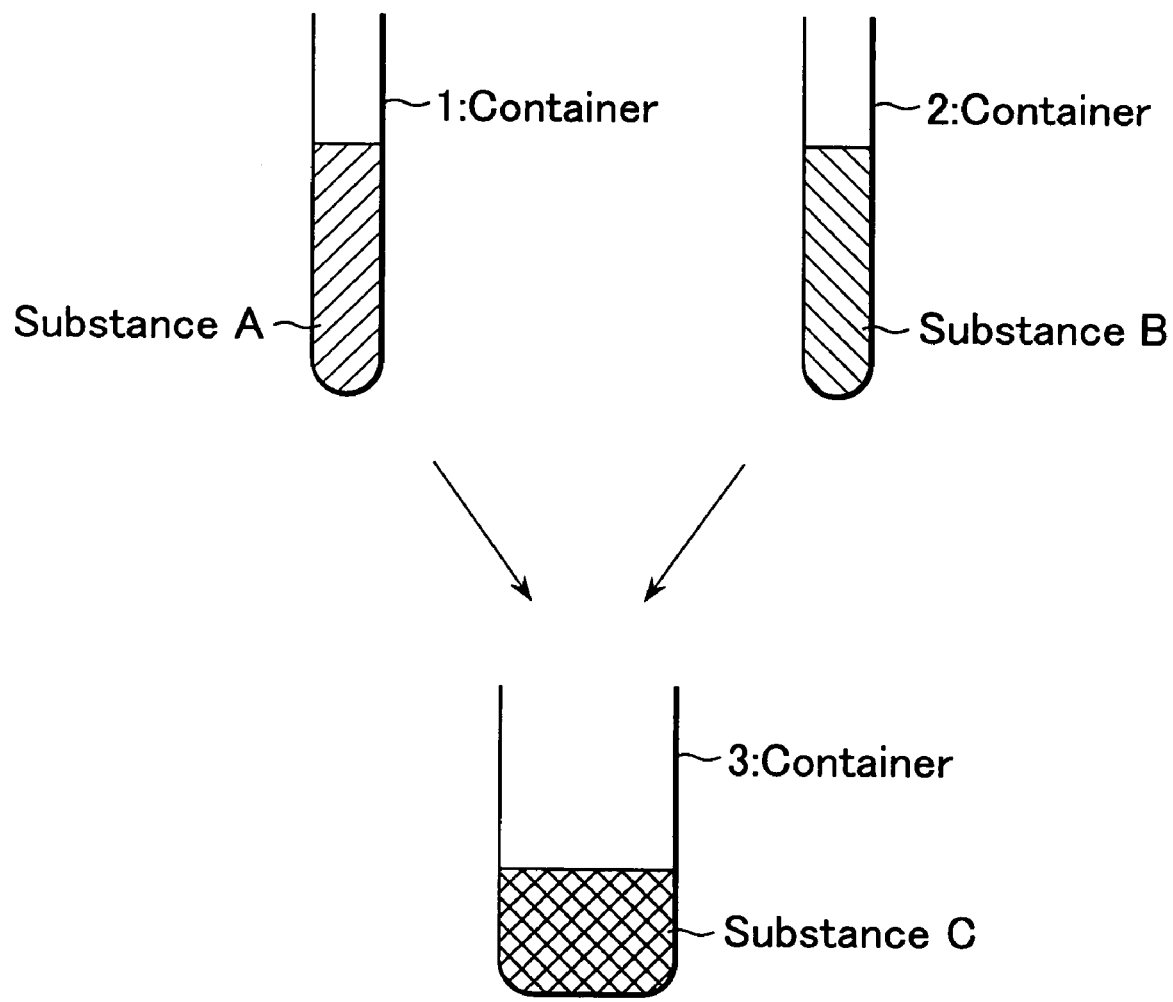

Hexagon

Rhombus

Circular form

Sealed along both sides of the flow path

FIG.50A
FIG.50B
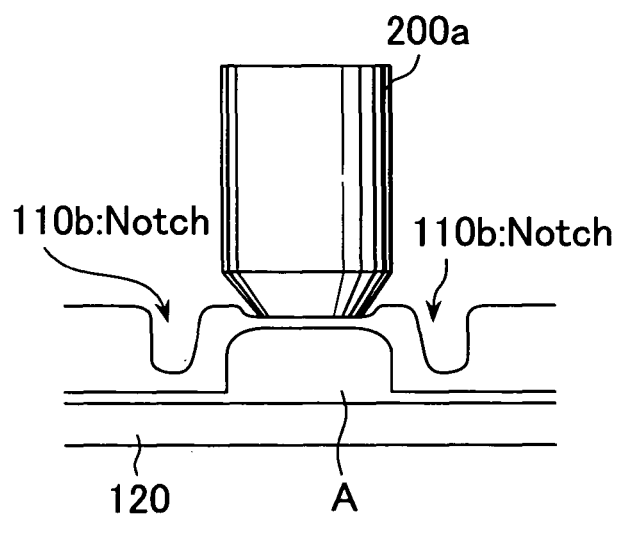
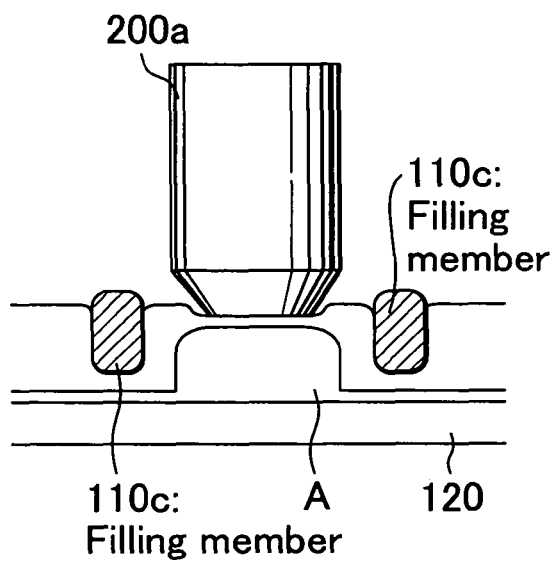
FIG.51
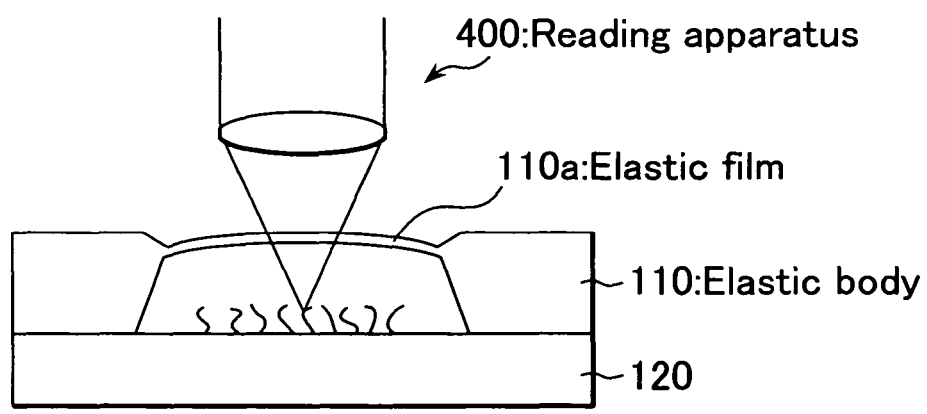

CHEMICAL REACTION CARTRIDGE, ITS FABRICATION METHOD, AND A CHEMICAL REACTION CARTRIDGE DRIVE SYSTEM

BACKGROUND OF THE INVENTION

1. Field of the Invention

The present invention relates to chemical reaction cartridges, more particularly, the chemical reaction cartridges wherein synthesis, dissolution, detection, separation or the like of solution can be performed easily according to prescribed protocols without differences among operators at low cost.

2. Description of the Prior Art

Conventionally, test tubes, beakers, pipettes or the like have been generally used for processing such as synthesis, dissolution, detection, separation or the like of solution. For example, as shown in FIG. 1, substance A and substance B are collected in container 1 and container 2 respectively such as test tubes or beakers. Then, these substances are added to container 3 such as a test tube or a beaker, wherein these substances are mixed or disturbed to create substance C. Substance C synthesized in this manner is observed, for example, in terms of light emission, heat generation, color change, color comparison, or the like.

Alternatively, a mixed substance is percolated, centrifugally separated or the like to separate and extract a target substance.

Also, glassware such as a test tube or a beaker is used for treatments such as dissolution, for example, by means of organic solvent. Also in the case of detection processing, as in FIG. 1, substance A under test in container 1 and a reagent in container 2 are injected into container 3 to observe their reaction results.

On the other hand, for devices such as bioanalyzers, for example, bags formed in a flat pouch shape using flexible materials as described in the Japanese Unexamined Patent Application No. 2002-365299, are used.

FIG. 2 is a configuration drawing of a biochip as described in the above-mentioned Japanese Unexamined Patent Application No. 2002-365299. FIG. 2(a) is a cross-sectional view. FIG. 2(b) is a plan view. The center part of flat blood collection bag 41 which is sealed at its periphery is in a pisciform pouch. The opening of the pisciform pouch is sealed with rubber plug 42.

In blood collection bag 4l, collection block 43, preprocessing area 44, junction 45, and waste liquid reservoir 47 are formed in order from this plug 42 towards the back. For blood collection, plug 42 is inserted into a syringe (not illustrated), wherein a syringe needle is projected to penetrate plug 42.

For blood collection, plug 42 is inserted into a syringe (not illustrated). A syringe needle is projected in the syringe to penetrate plug 42.

For blood collection, the tip of the needle projected externally from the syringe is inserted into a person under test. Hooks 52 and 53 of blood collection bag 41 are pulled out to collect blood in collection block 43. After blood collection, the syringe is withdrawn from blood collection bag 41. Then, as shown in FIG. 3, blood collection bag 41 is sandwiched between rotating rollers 61 and 62 to squash the biochip from collection block 43 towards preprocessing area 44. The collected blood is sent to preprocessing area 44.

When rollers 61 and 62 proceed and start squashing pocket 48, solution in pocket 48 breaks valve 49 and flows into preprocessing area 44. Next, solution in pocket 50 flows into preprocessing area 44 in the same manner. When the prescribed processing in preprocessing area 44 ends, the rollers are rotated to send the processed blood to junction 45.

DNA chip 46 is arranged in junction 45 to perform hybridization. The extra blood or solution pressed out from preprocessing area 44 is stored in waste liquid reservoir 47. Conditions of DNA chip 46 wherein hybridization is performed are observed by means of a reading apparatus arranged externally.

However, conventional methods using beakers, pipettes or the like have problems such as complicated operations, large differences among operators, and a large amount of time and effort required.

In addition, blood collection bags have the problem that it is not easy to move solution because these bags lack elasticity.

SUMMARY OF THE INVENTION

An object of the present invention is to realize a chemical reaction cartridge, which enables prescribed protocols to be achieved easily without differences among operators, is sealed and disposable, and has a safe structure against viruses or dangerous drugs, as well as to realize its fabrication method and a chemical reaction cartridge drive system.

BRIEF DESCRIPTION OF THE DRAWINGS

FIG. 1 illustrates a prior art processing method.

FIG. 50 illustrates a principal portion of yet another embodiment of the present invention.

FIG. 51 illustrates a principal portion of yet another embodiment of the present invention.

DETAILED DESCRIPTION OF THE PREFERRED EMBODIMENTS

Figure 2A:
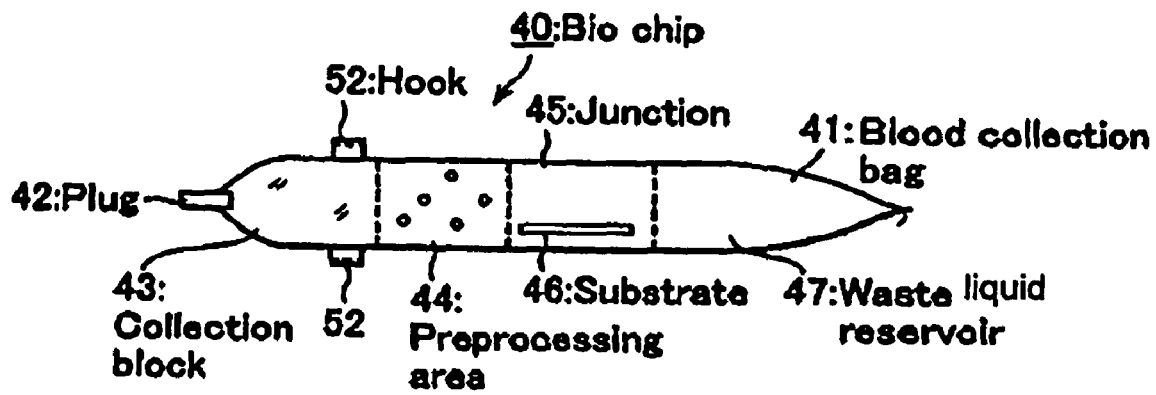
FIG. 2 is a configuration diagram of a prior art blood collection bag.
Figure 2B:
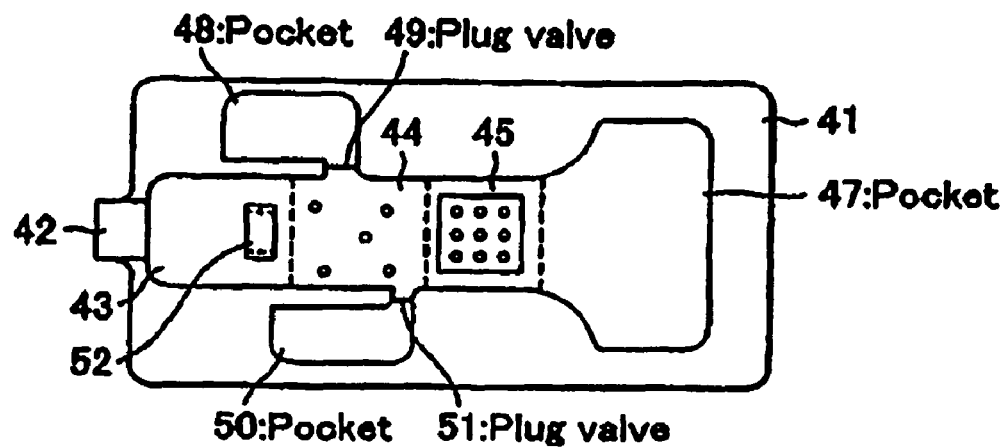
Figure 3:
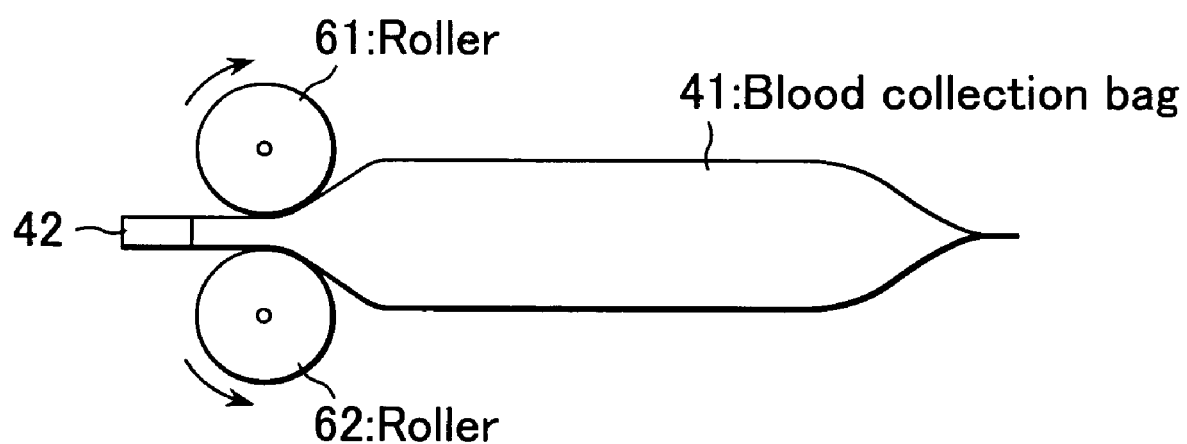
FIG. 3 illustrates an operation method of the blood collection bag.
Figure 4A:
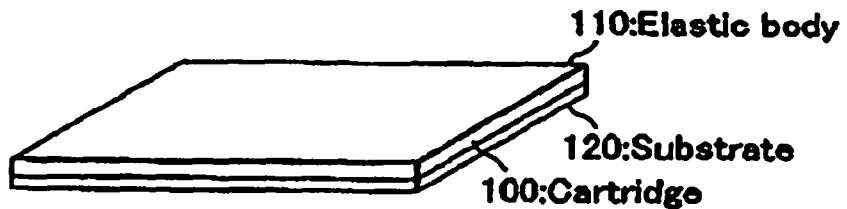
FIG. 4 is a configuration diagram of an embodiment of a chemical reaction cartridge concerning the present invention.
Figure 4B:
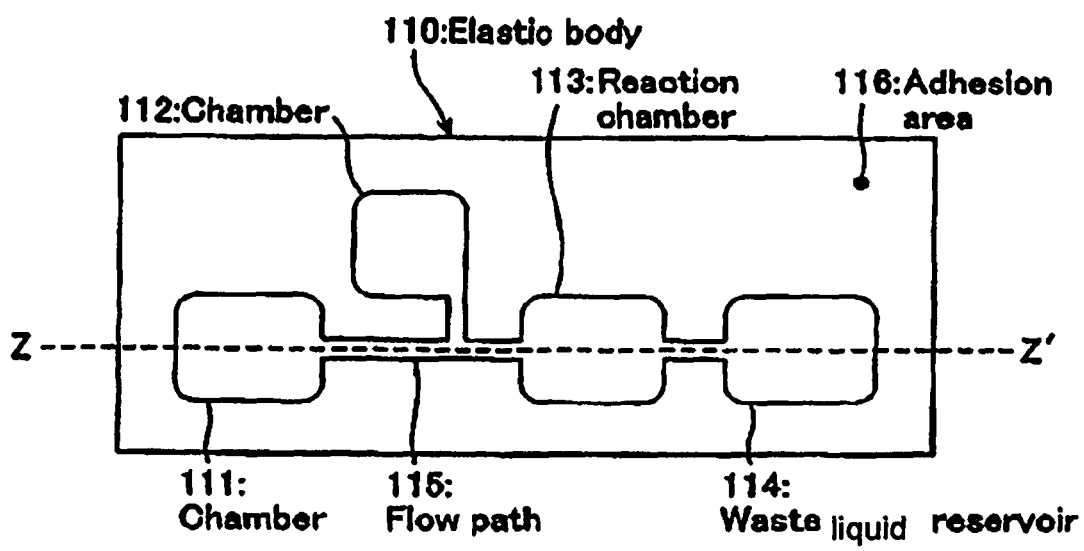
Figure 4C:
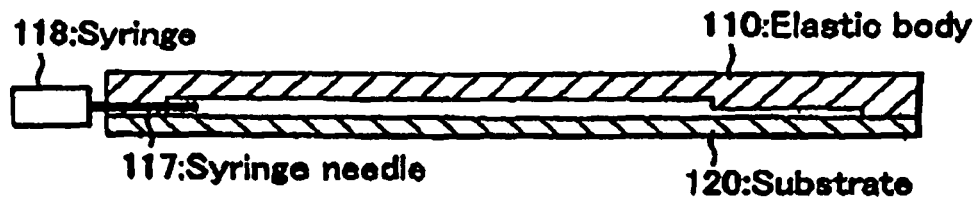

The present invention is now explained in detail with reference to the drawings. FIG. 4 is a configuration diagram of an embodiment of a chemical reaction cartridge concerning the present invention. FIG. 4(a) is a perspective view. FIG. 4(b) is a bottom view of an elastic body. FIG. 4(c) is a Z-Z' cross-sectional view. Chemical reaction cartridge 100 comprises elastic body 110 made of sealed elastic rubber or the like and tabular substrate (rigid body substrate) 120 made of hard materials for the purpose of position determination and shape maintenance.

A viscoelastic body or a plastic body may be used for elastic body 110 for a cartridge (however, an elastic body is used as an example of the embodiment).

Holes for solution (hereinafter called "chamber") 111 and 112, each of which is concave towards the surface, a chamber for reaction (also called "a reaction chamber") 113, a chamber for storing waste liquid (also called "a waste liquid reservoir") 114, and a flow path 115 linking these chambers are formed on the back of elastic body 110, as shown in FIG. 4(b).

Elastic body 110 and tabular adhesion area 116 excluding the flow path are adhered to the surface of substrate 120, as shown in FIG. 4(c), thereby creating a structure wherein chambers and the flow path are sealed by elastic body 110 and substrate 120 to prevent solution from leaking externally.

Next, transfer of solution in a cartridge with such a structure is explained. Substance (hereinafter called "solution" because solution is used as an example) A and solution B are injected in advance into chambers 111 and 112, which are formed on cartridge 100. Solution is injected by means of syringe 118 after syringe needle 117 is directly inserted into elastic body 110, as shown in FIG. 4(c). Since elastic body 110 is formed of elastic materials, the needle hole self-closes if syringe needle 117 is withdrawn. In order to seal the hole completely, the needle hole is filled with adhesive agent or the like after solution is injected. However, the hole may be sealed by means of heated dissolution.

Figure 5:
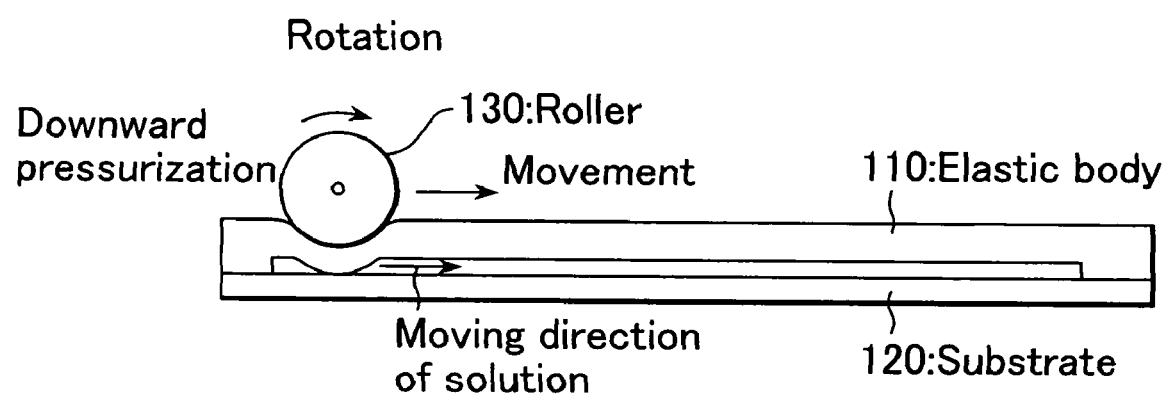
FIG. 5 illustrates an operating state.
Figure 6A:
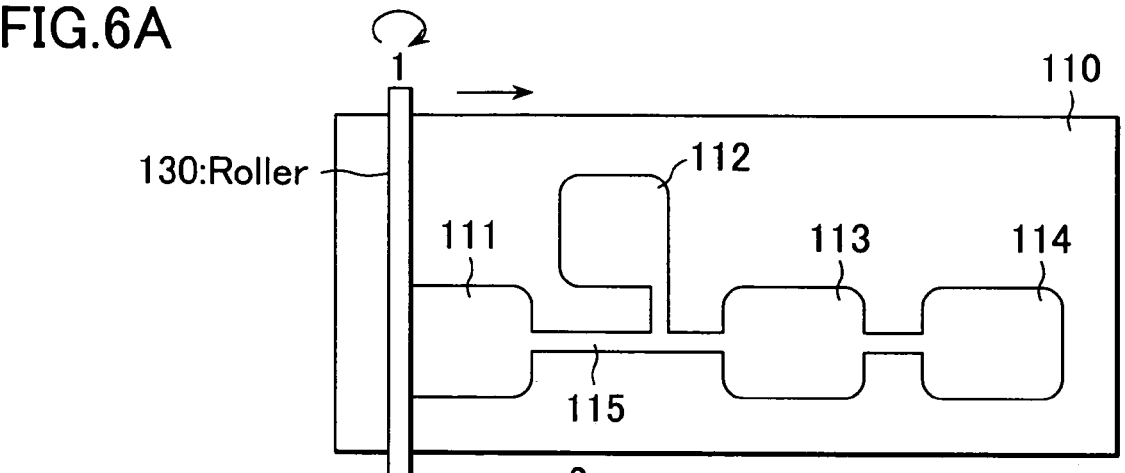
FIG. 6 exemplifies another operating state.

As FIG. 5 shows, roller 130 is pressed downward from above at the left end of cartridge 100 to the extent that chamber 111 is squashed. Then, if roller 130 is rotated and moved from position 1 to the right direction as shown in FIG. 6(a), solution A stored in chamber 111 is pressed out to the right direction. Solution A is sent through flow path 115 into reaction chamber 113. The air in chamber 113 is sent out to waste liquid reservoir 114.

Figure 6B:
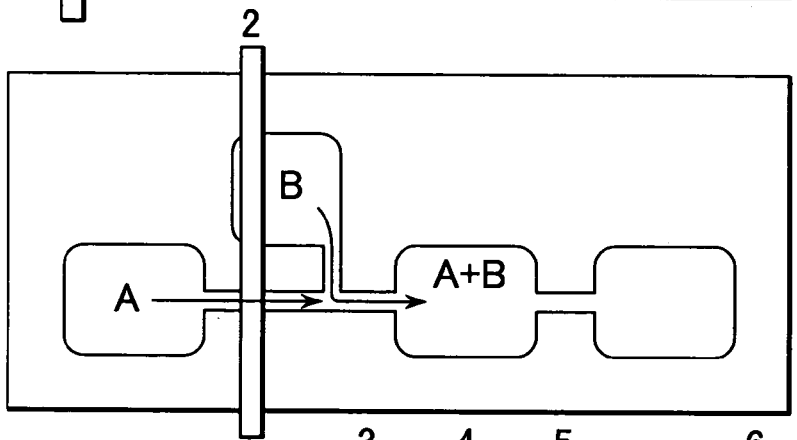

If roller 130 is continuously rotated and moved to position 2 as shown in FIG. 6(b), solution B in chamber 112 is sent out. Solution B is pressed out through flow path 115 into reaction chamber 113. On this occasion, the halfway portion of flow path 115 is also squashed when roller 130 is pressed downward, which in turn becomes a valve to stop flow-back, thereby preventing solution B from flowing back to chamber 111.

When solution A and solution B enter reaction chamber 113, they are mixed and react. Reaction here means, for example, mixture, synthesis, dissolution, separation or the like.

Use of these cartridges enables detection of, for example, dioxin, DNA or the like.

Figure 6C:
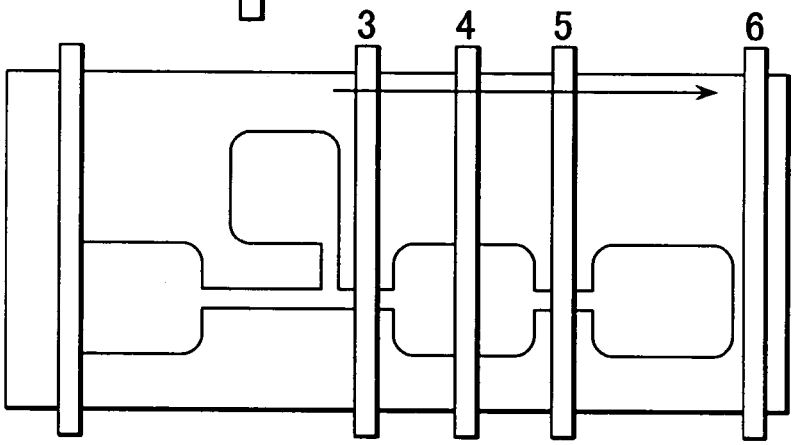
Figure 6D:
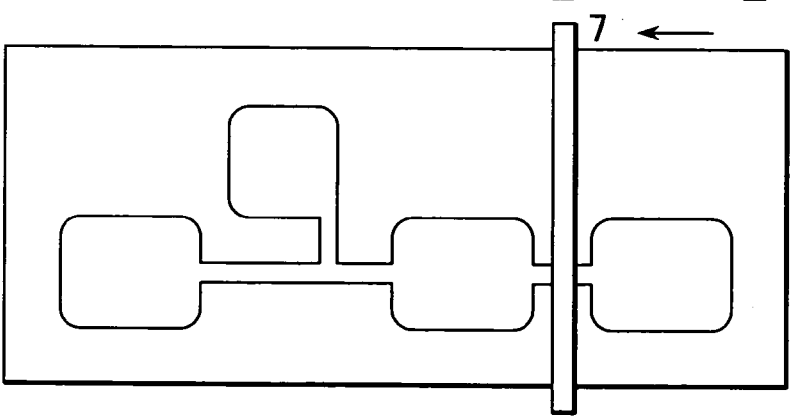

In addition, if roller 130 is rotated and moved to position 7 in the reverse direction as shown in FIG. 6(d) after roller 130 is rotated and moved from position 3 to position 6 as shown in FIG. 6(c), solution can be easily mixed.

Usually, roller 130 ends a rotary movement in one direction (in one path).

These cartridges can be fabricated to be small in size, light in weight and low in cost. Also, treatment protocols such as mixture, synthesis, dissolution, separation or detection of substances can be performed easily in these cartridges without differences among operators.

In addition, a cartridge of the present invention is sealed and disposable. It can handle viruses, dangerous drugs or the like safely. For example, treatments (a series of treatments such as neutralization, distillation, sampling, mixing, and calorimetric detection) of waste water from factories, concentration waste water or detection of cyanogen in rivers or the like into which such waste water flows, extraction of DNA or protein from blood streams or diseased parts, or the like can be performed in this cartridge safely and reliably.

Figure 7:
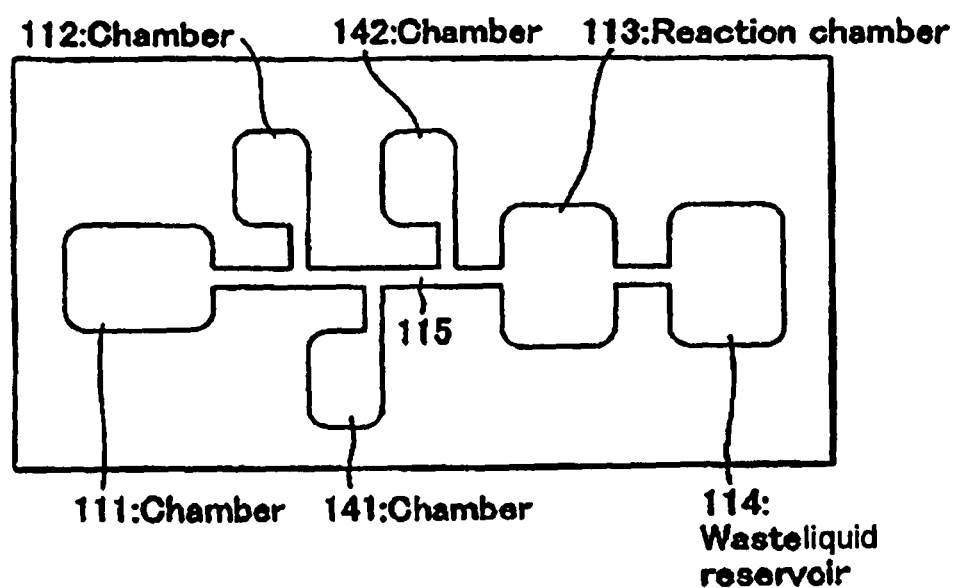
FIG. 7 is a configuration diagram of another embodiment of the present invention.

Note that these explanations are only intended to show certain appropriate embodiments in order to exemplify the present invention. Therefore, it is to be understood that the present invention is not restricted to the foregoing embodiments. Rather, many other alterations and modifications thereof may be made without departing from the spirit and essential characteristics thereof:

(1) As shown in FIG. 7, not only chambers 111 and 112 for solutions A and B respectively but also chambers 141 and 142 leading to flow path 115 may be formed for the purpose of storing cleaning liquid or drying air.

Figure 8:
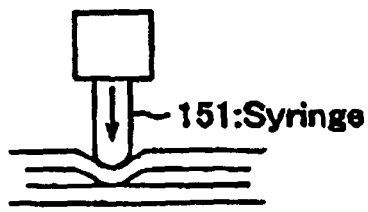
FIG. 8 illustrates an embodiment concerning a flow path pressurization method.

(2) Downward pressurization of the flow path by means of an external force outside a cartridge may be performed not only by a roller but also by an actuator which applies force in a vertical direction to syringe 151 as shown in FIG. 8, wherein chamber 112 shown in FIG. 7 or the like may also be pressed directly by the actuator so that solution in chamber 112 can be pressed out.

Figure 9:
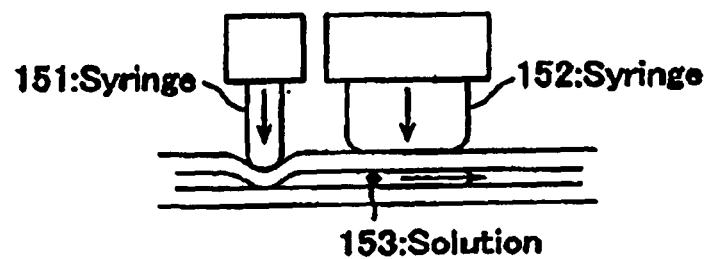
FIG. 9 illustrates another embodiment concerning a flow path pressurization method.

(3) As shown in FIG. 9, a plurality of actuators may be used to realize pumping, wherein solution 153 can be pressed out into the direction of the arrow (right) if wide syringe 152 is pressed down after syringe 151 is pressed down.

Figure 10:
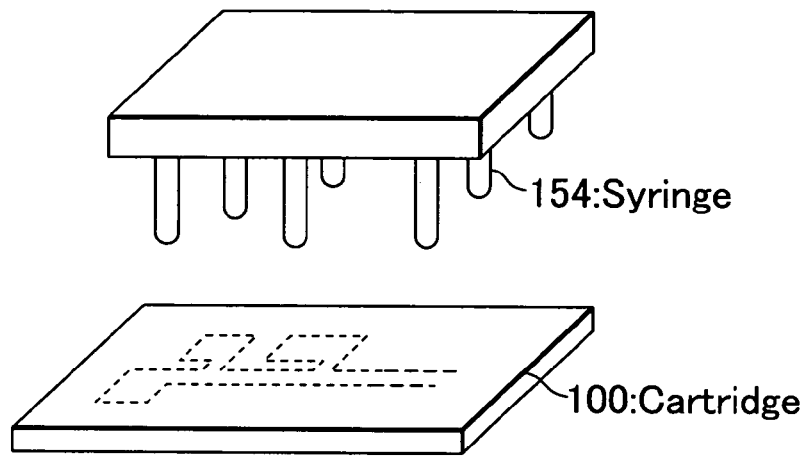
FIG. 10 illustrates yet another embodiment concerning a flow path pressurization method.

(4) As shown in FIG. 10, if a plurality of actuators with capability to control individual actions are arranged in a matrix and are pressed down, they can also be used for cartridges with general-purpose flow paths.

Figure 11A:
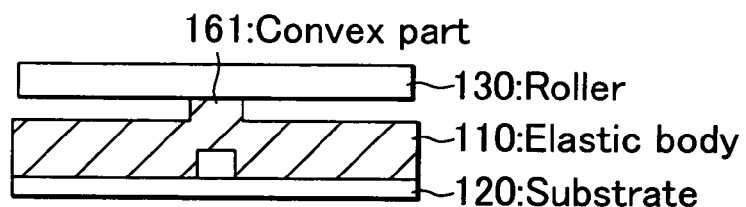
FIG. 11 is a configuration diagram of yet another embodiment of the present invention.
Figure 11B:
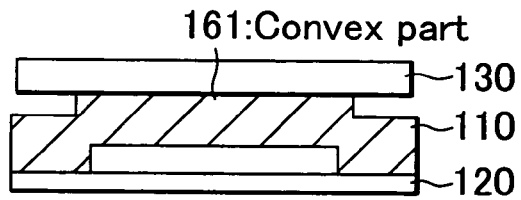
Figure 11C:
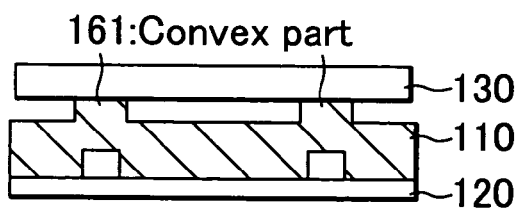

(5) Convex part 161 is formed on the surface of elastic body 110 immediately above a flow path, as shown in FIGS. 11(a), (b), and (c). Even if widths, shapes or the number of flow paths change, they can be squashed and sealed reliably, where in rigid substrate 120 is very helpful in maintaining positions accurately.

Figure 12A:
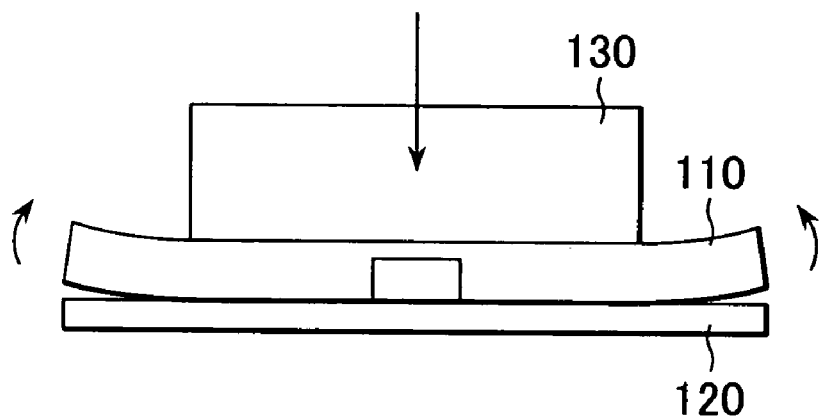
FIG. 12 illustrates a pressurization method.
Figure 12B:
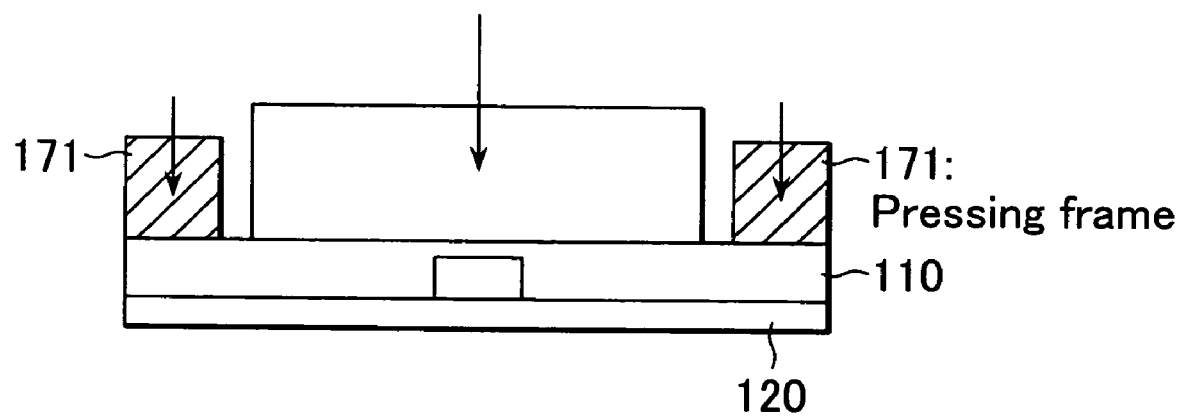

(6) If the width of a roller is smaller than that of a cartridge, peripheral areas of elastic body 110 may tend to camber as shown in FIG. 12(a), wherein peripheral areas should be pressed in advance by means of pressing frame 171 as shown in FIG. 12(b).

Figure 13A:
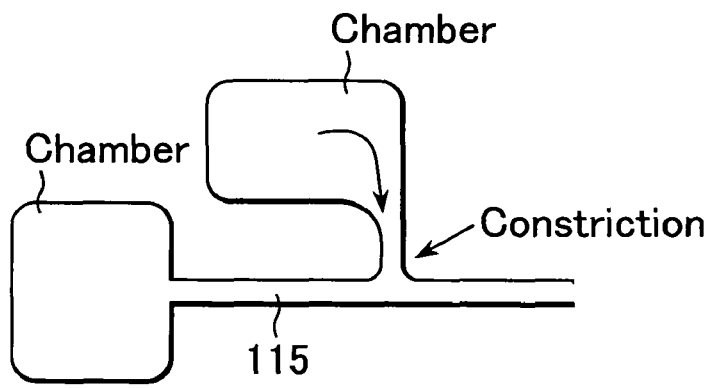
FIG. 13 illustrates a concrete example of a shape of a flow path.
Figure 13B:
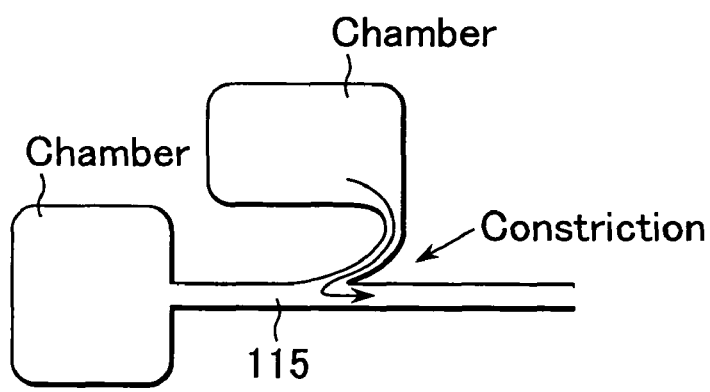
Figure 13C:
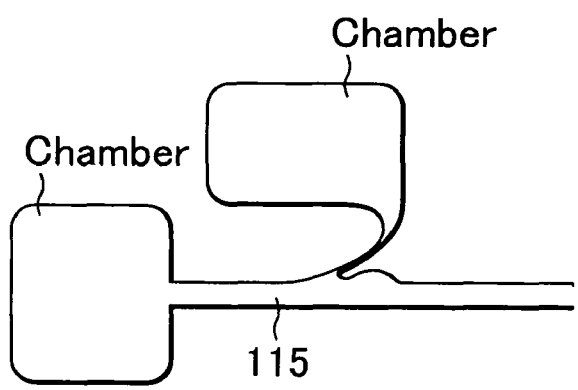
Figure 13D:
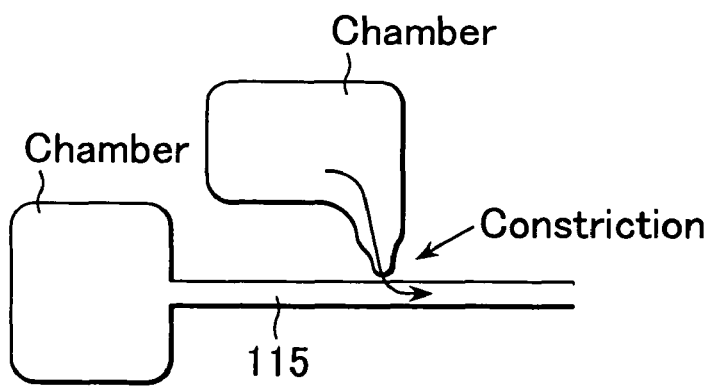

(7) As shown in FIG. 13(a), a substantially narrow connecting part between a chamber of elastic body 110 and a flow path is formed, which makes it easier for solution in the chamber to exit, but which does not allow solution in the flow path to enter the chamber due to such factors as viscosity resistance. Or, as shown in FIG. 13(b) or (c), a film valve may be formed for the connecting part. Or, as shown in FIG. 13(d), the valve may be broken by the pressure of solution in the chamber so that the solution is pressed out.

Figure 14:
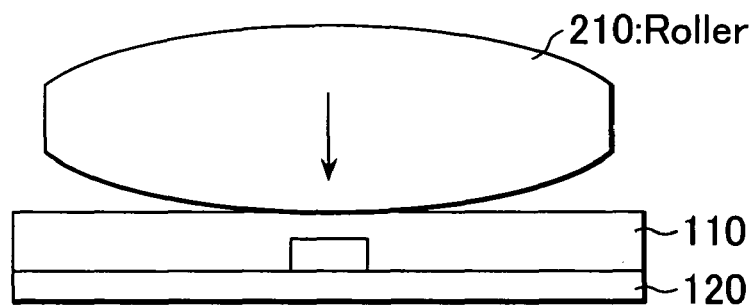
FIG. 14 illustrates another pressurization method.
Figure 15:
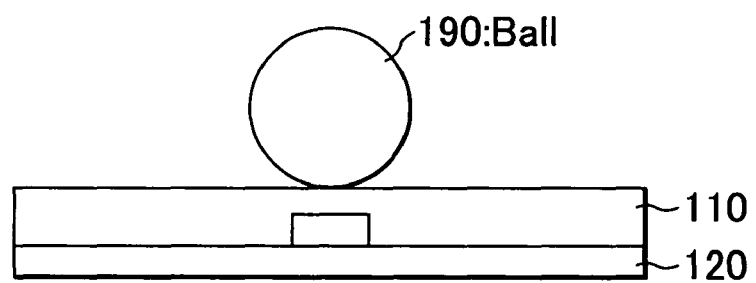
FIG. 15 illustrates yet another pressurization method.
Figure 16:
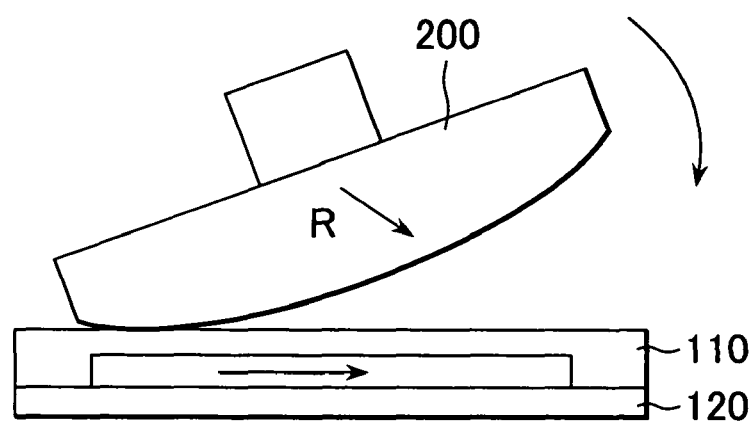
FIG. 16 illustrates yet another pressurization method.

(8) Pressurization member 180 with the shape of its center expanding (curved) like a barrel may be used instead of a cylindrical roller, as shown in FIG. 14. Or, as shown in FIG. 15, pressurization member 190 in a ball shape may be used. Or, as shown in FIG. 16, pressurization member 200 based on an absorbent blotting paper method in a circular arc shape of a large radius of curvature may be used. Solution can be pressed out in the direction of the arrow if pressurization member 200 is rotated in the right direction as shown in FIG. 16.

Figure 17A:
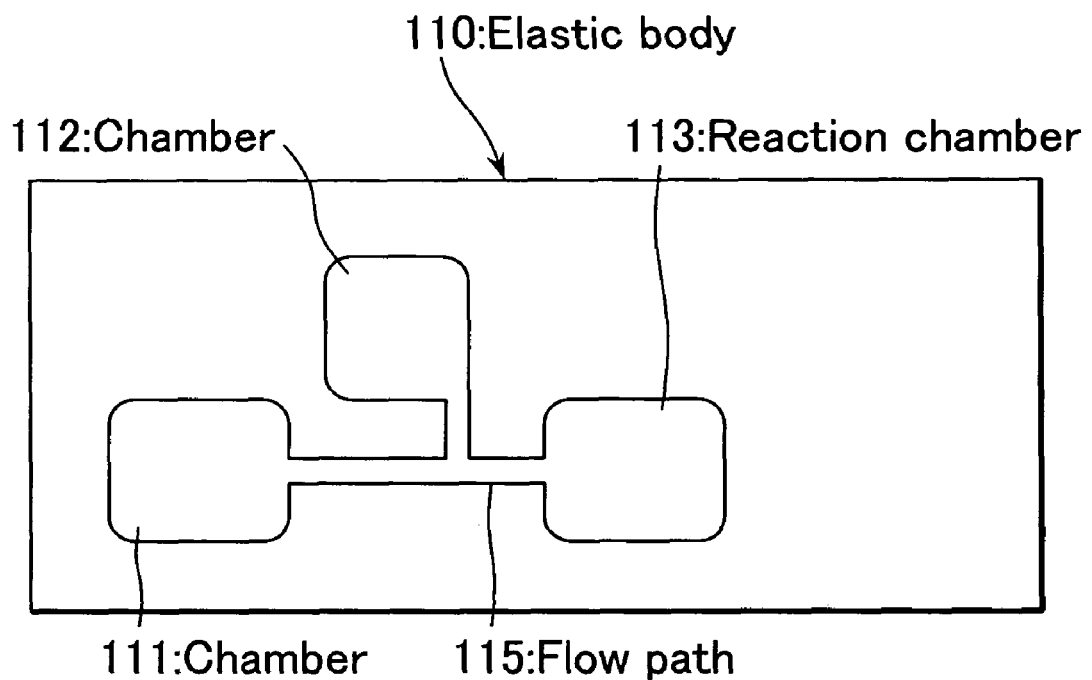
FIG. 17 is a configuration diagram of yet another embodiment of the present invention.
Figure 17B:
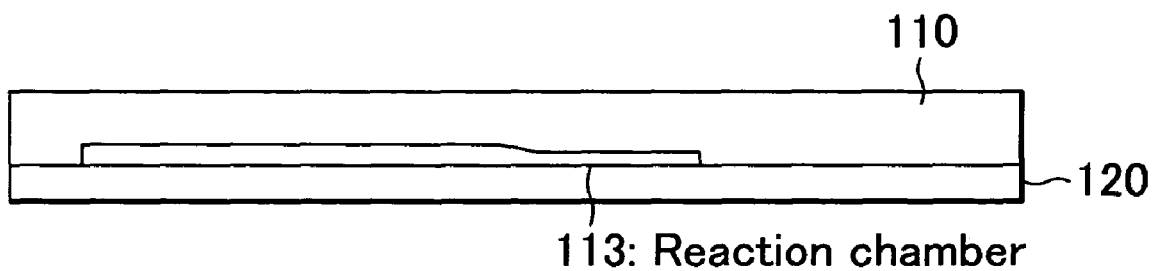

(9) As shown in FIG. 17(a), if reaction chamber 113 is formed thinly from the beginning to expand in the thickness direction when pressure is applied, there is no need to drain the air of reaction chamber 113. Thus, a chamber for storing waste liquid does not have to be provided in elastic body 110 of cartridge 100.

Figure 18A:
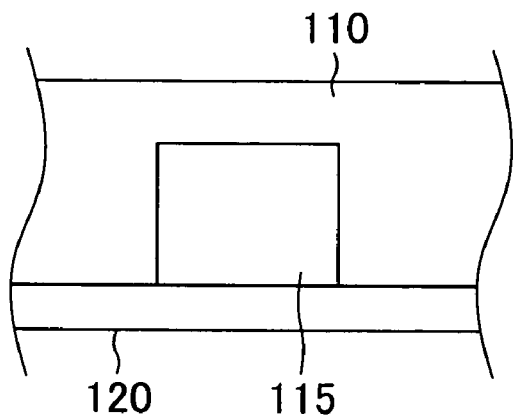
FIG. 18 illustrates a shape of a flow path or a chamber.
Figure 18B:
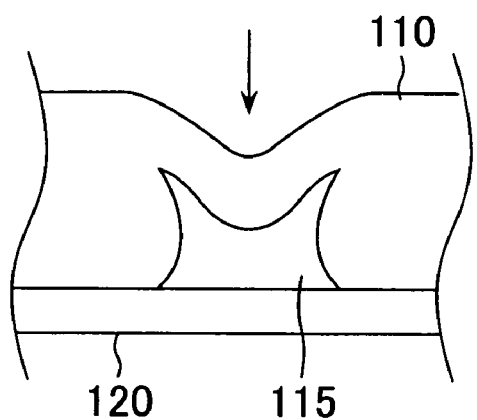
Figure 18C:
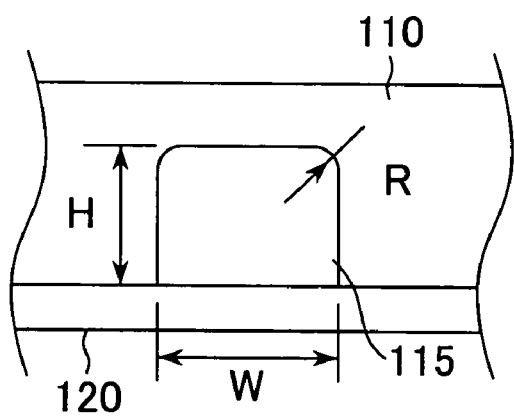
Figure 18D:
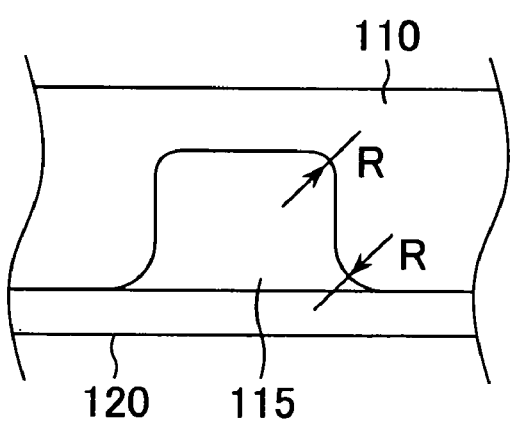

(10) With respect to the cross-sectional shape of flow path 115 (or a chamber), if corners are right-angles as shown in FIG. 18(a), flow path 115 is squashed when pressed from above as shown in FIG. 18(b), while solution tends to remain at the corners. Thus, as shown in FIG. 18(c), the corners are provided with a curvature of a radius R. If flow path 115 has a height H and a width W, R is desirably one-tenth or more of H or W. As shown in FIG. 18(d), it is desirable that a corner of a joint with substrate 120 should also have a curvature of radius R, as shown in FIG. 18(d).

(11) The wall surface of flow path 115 may be given a surface treatment to provide a hydrophobic surface if solution is soluble in water or to provide a hydrophilic surface if solution is oily, so that adhesion of solution is prevented. Or, Teflon (registered trademark) coating may be provided, or Teflon (registered trademark) rubber may be used as materials for elastic body 110.

Figure 19A:
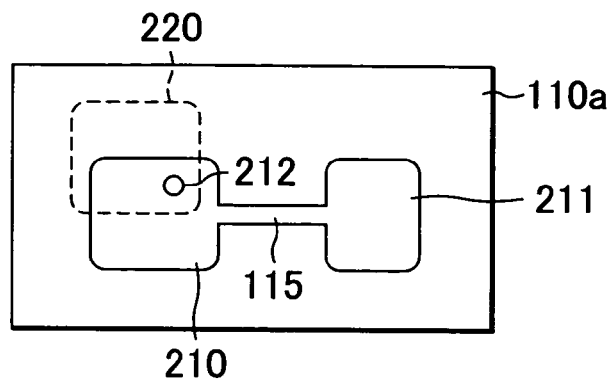
FIG. 19 illustrates an elastic body having a layered structure.
Figure 19B:
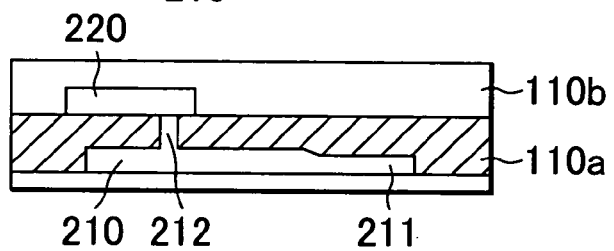

(12) Elastic body 110 may have two or more layers. For example, as FIG. 19 schematic drawing shows (FIG. 19(a) is a bottom view of elastic body 110 and FIG. 19(b) is a cross-sectional view of elastic body 110), chambers 210 and 211 are formed in the first layer 110a, while chamber 220 is formed in the second layer 110b. In addition, flow path 212 is formed for chamber 210 of the first layer 110a for connection to chamber 220 of the second chamber 110b, thereby making chambers three-dimensional in a compact manner.

(13) Reaction chamber 113 is formed so that it is possible to detect light, voltage, current, heat or the like of reaction substances. For example, a whole elastic body is made transparent or non-transparent (opaque) to light. Or, only an optical measurement portion is made transparent. If portions other than the optical measurement portion are made opaque, reagents stored in chambers are protected against light. Or, the whole elastic body may be formed of an insulating body wherein a portion is formed of a conductive elastic body (containing carbon or the like).

Figure 20A:
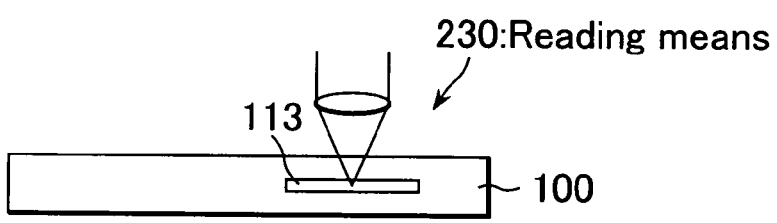
FIG. 20 illustrates a detection method of a reaction chamber.

In order to observe light emitted from a reaction substance, as shown in FIG. 20(a), elastic body 110 is formed of transparent materials wherein observations are conducted by reading means 230, which reads light emitted from the reaction substance. Elastic body 110 does not have to be transparent entirely. Instead, it is sufficient that only an optical measurement portion is transparent. Here, a glass chamber or the like can be embedded.

Figure 20B:
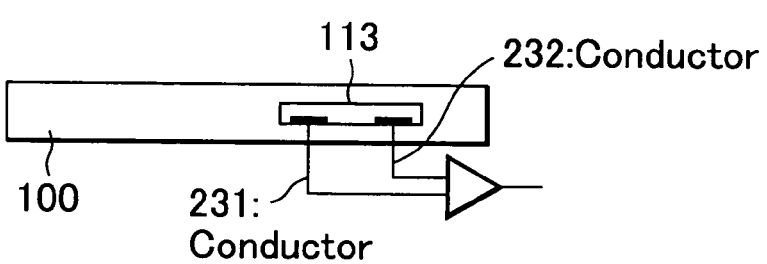
Figure 20C:
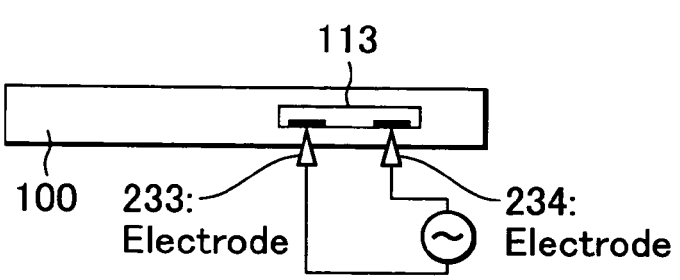

If voltage or current is detected or if electrophoresis is conducted, as shown in FIG. 20(b), conductors 231 and 232 are arranged to pick up detection signals directly from reaction chamber 113. Or, as shown in FIG. 20(c), electrodes 233 and 234 may be inserted from outside when necessary.

Figure 21:
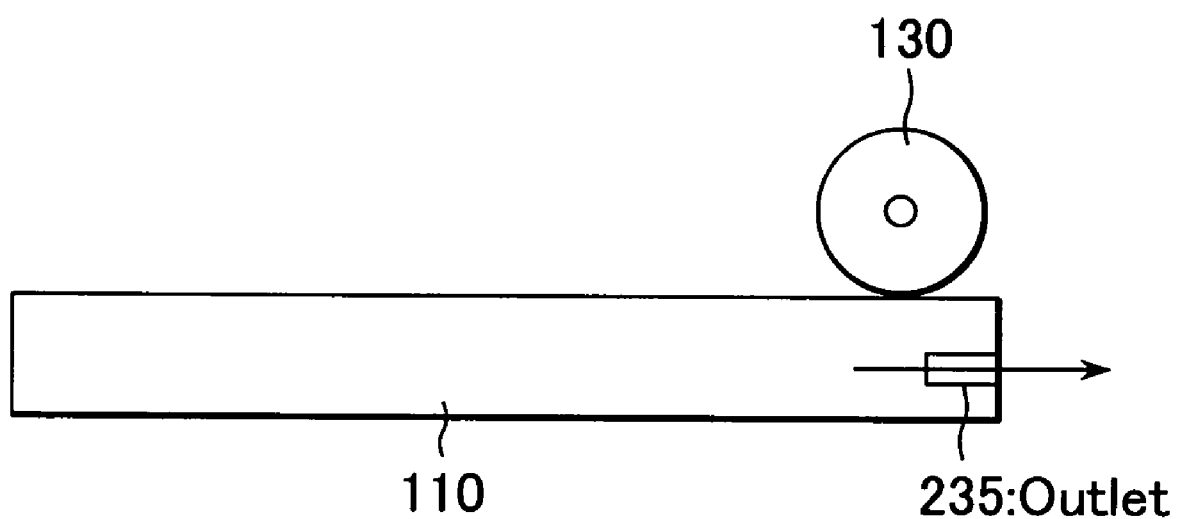
FIG. 21 is a configuration diagram of yet another embodiment of a cartridge.

(14) As shown in FIG. 21, outlet 235 is provided for elastic body 110 in order to establish a structure wherein a reaction substance can be pressed out from outlet 235 to the outside by means of downward pressurization of roller 130. In this case, it is desirable that only safe substances should be used as reaction substances to be drained.

Figure 22:
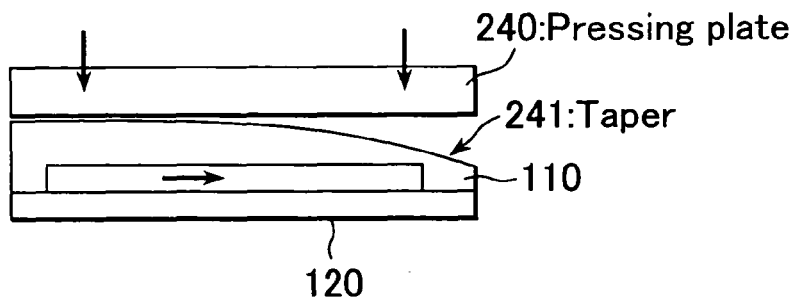
FIG. 22 is a configuration diagram of yet another embodiment of a cartridge.

(15) As shown in FIG. 22, taper 241 in a circular arc shape may be provided to the upper surface of elastic body 110, wherein solution is sent out in the direction of the arrow if tabular pressing plate 240 is vertically pressed down from above.

Figure 23:
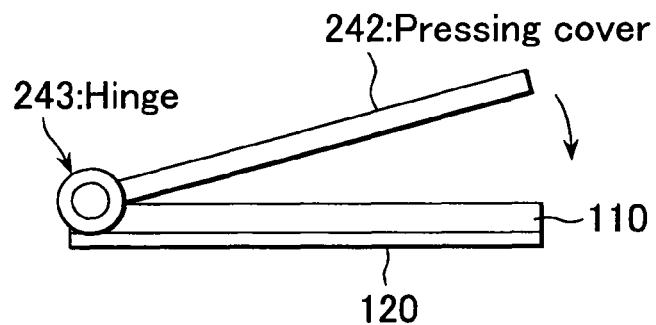
FIG. 23 is a configuration diagram of yet another embodiment of a cartridge.

(16) As shown in FIG. 23, pressing cover 242 and substrate 120 can be joined by means of hinge 243 so that pressing cover 242 can be freely opened or closed, thereby being able to send out solution when pressing cover 242 is closed.

Figure 24A:
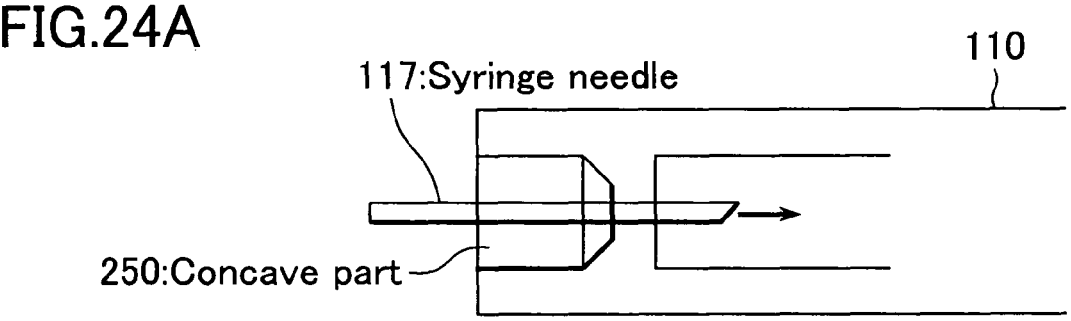
FIG. 24 is a configuration diagram of an embodiment of an inlet of a cartridge.
Figure 24B:
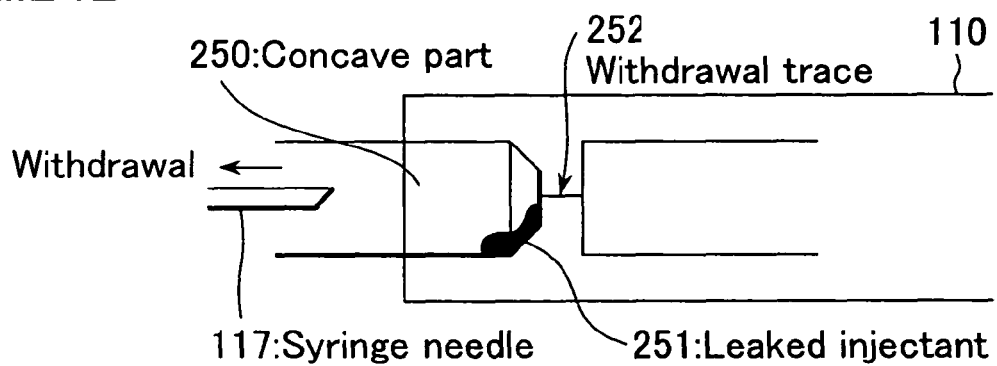

(17) Concave part 250 is formed at an inlet for injecting samples as shown in FIG. 24. When syringe needle 117 is inserted or withdrawn, an injectant is leaked and adhered to the injection inlet. However, as shown in FIG. 24(b), leaked injectant 251 remains in the back of concave part 250 due to the injectant's viscosity or surface tension and cannot be drained out of the cartridge. This is useful when injection liquid (such as blood) itself is hazardous. Withdrawal trace 252 of syringe needle 117 is automatically closed.

(18) An elastic body is made of materials such as silicone rubber, PDMS (polydimethylsiloxane), natural rubber and its polymer, acrylic rubber, urethane rubber, or the like. These materials do not have to be perfectly elastic bodies and can be resins having viscoelastic characteristics or plastic bodies such as gel. If a material deforms almost plastically, it is difficult for a gap to be caused even in the case of FIG. 18(b).

Figure 25A:
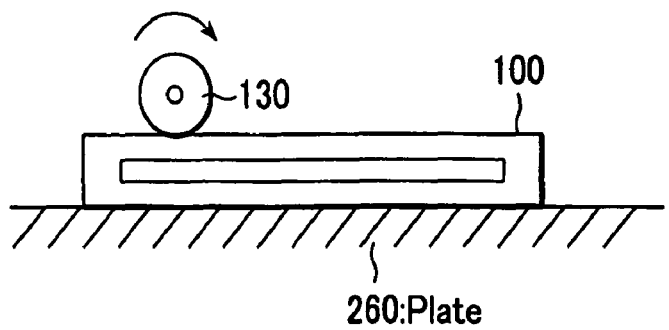
FIG. 25 is a diagram related to the materials of a substrate.
Figure 25B:
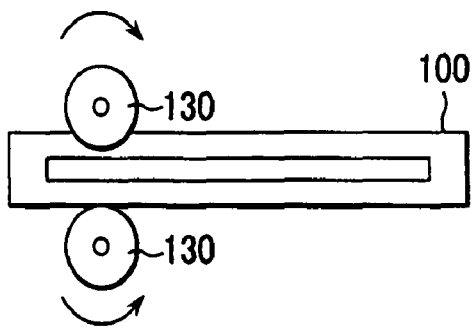

(19) As materials for substrate 120, glass, metals, hard resins, rigid bodies that can be bent, or the like can be used. If a rigid body which can be bent is used, a cartridge is placed on a hard plate or table 260 to use roller 130 for applying pressure or cartridge 100 is sandwiched between two rollers 130 from above and from below, as shown in FIG. 25(a) and FIG. 25(b).

(20) In order to seal an injection inlet after solution is injected into chamber 111, chamber 112, or the like, heat or adhesive agent can be used.

Figure 26A:
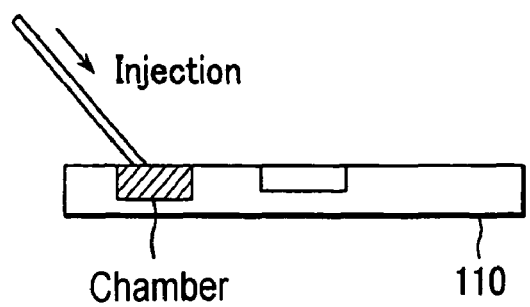
FIG. 26 illustrates a method concerning injection and junction.
Figure 26B:
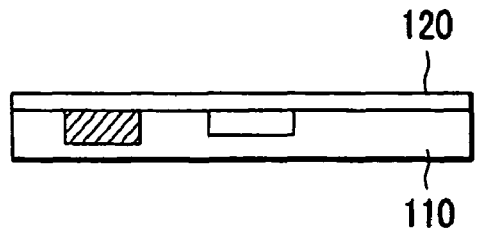

Or, as shown in FIG. 26(a) and FIG. 26(b), elastic body 110 is placed upside down, wherein a chamber is turned upward and solution is injected into the chamber. After that, substrate 120 is used to cover the chamber, as shown in FIG. 26(b).

(21) Elastic body 110 and substrate 120 can be joined by means of absorption (in the case of PDMS, glass or the like), ultrasonic wave, heating, plasma treatment, vibration or the like, in addition to adhesion.

(22) Substances applicable to testing in cartridges are biological molecules, organic matters, inorganic matters or living organisms such as bacteria, diseased parts, cells or the like.

(23) For extraction processing in a reaction chamber, magnetic beds, silica beads, silica filters, monolith filters, antibodies, enzymes, dendrimers or the like can be used as extraction means. Note that vibration to disperse magnetic beads is given by a source of vibration, which is applied, for example, to the outside of a cartridge.

(24) For safety, it is desirable that a solidification reactant should be injected into a waste liquid reservoir in advance.

Figure 27A:
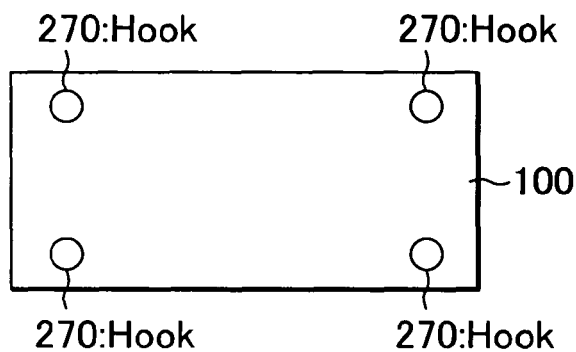
FIG. 27 is a configuration diagram of yet another embodiment of a cartridge.
Figure 27B:
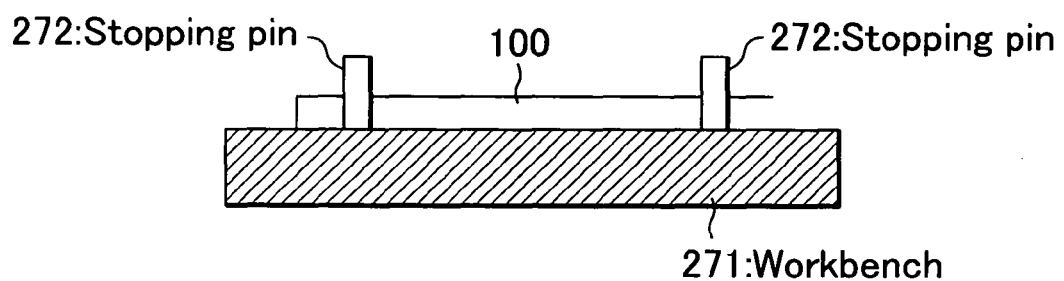

(25) Since a rigid substrate is affixed to a cartridge, it is possible to determine an accurate position when external force is applied or when measurements are conducted. Moreover, as shown in FIG. 27(a), a hook or hole 270 for the hook may be provided for fixing a position when a force is applied from outside. FIG. 27(b) is a side view (cross-sectional view) when a cartridge is fixed to workbench 271 in such a way that hole 270 in FIG. 27(a) is aligned to stopping pin 272 which is mounted to workbench 271.

Figure 28:
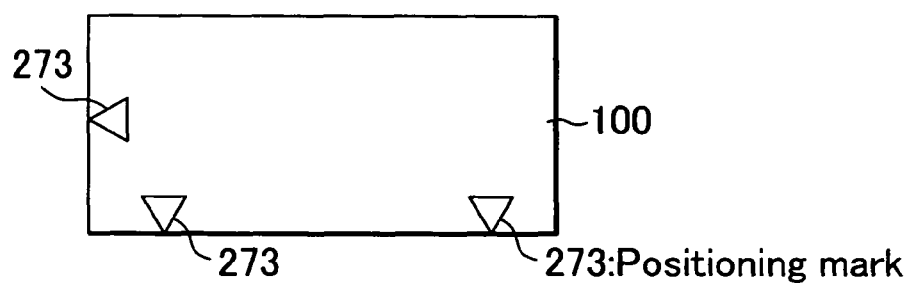
FIG. 28 is a configuration diagram of yet another embodiment of a cartridge.

In addition, as shown in FIG. 28, positioning mark 273 may be provided for such activities as measurements.

(26) Samples may be injected using roller 130 as shown in FIG. 29. In other words, as shown in FIG. 29(a), after syringe needle 117 is inserted, roller 130 pressed downward as in FIG. 29(b) is moved in rotation from the injection inlet towards the back, thereby enabling a sample to be sucked into chamber 111 [FIG. 29(c)].

Figure 29A:
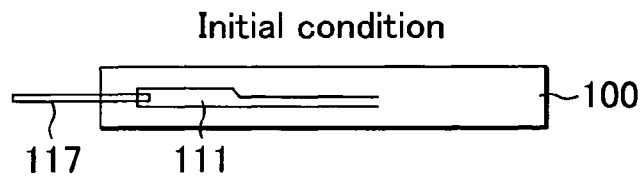
FIG. 29 illustrates a sucking method for samples.
Figure 29B:
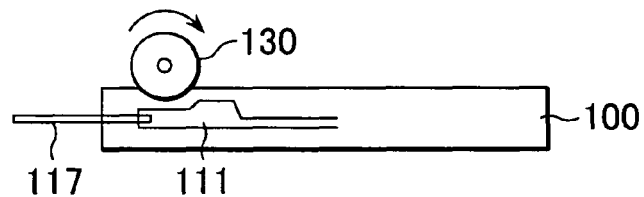
Figure 29C:
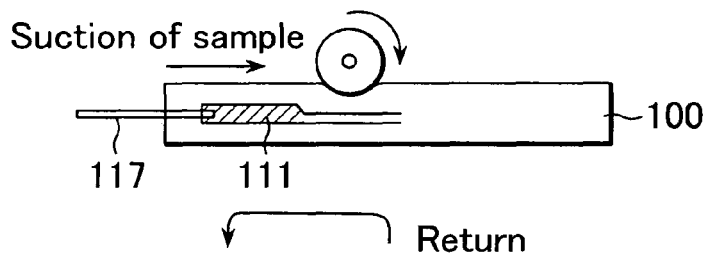
Figure 29D:
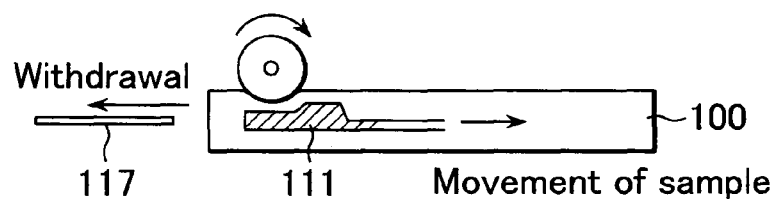

After the sample is sucked, syringe needle 117 is withdrawn as shown in FIG. 29(d), roller 130 is lifted upward and is returned to the original position, or a second roller separately provided is pressed, to send the sucked sample towards the back.

If the viscosity of the sample is large enough, the non-return valve effect of the roller is utilized at the position in FIG. 29(d) to send the sample in the cartridge, without withdrawing syringe needle 117.

Figure 30:
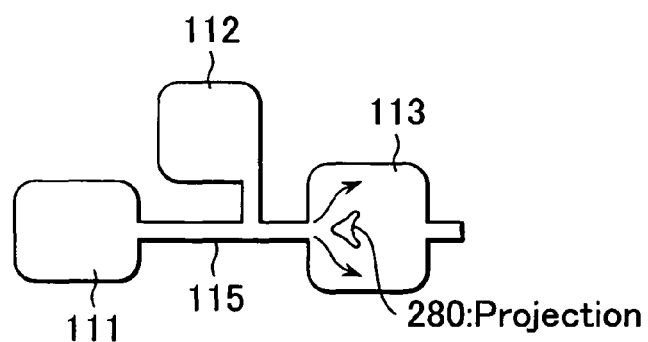
FIG. 30 is a configuration diagram of yet another embodiment of a cartridge.

(27) For the above-mentioned mixing, projection (or wall) 280 may be provided in chamber 113 for separation and disturbance as shown in FIG. 30.

Figure 31A:
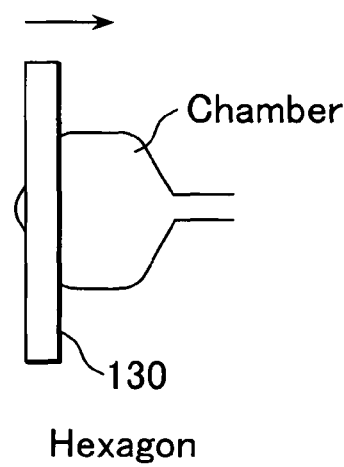
FIG. 31 illustrates an embodiment of a shape of a chamber.
Figure 31B:
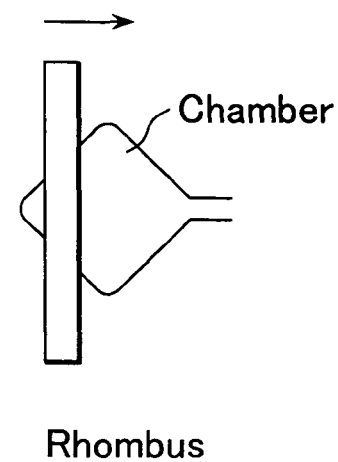
Figure 31C:
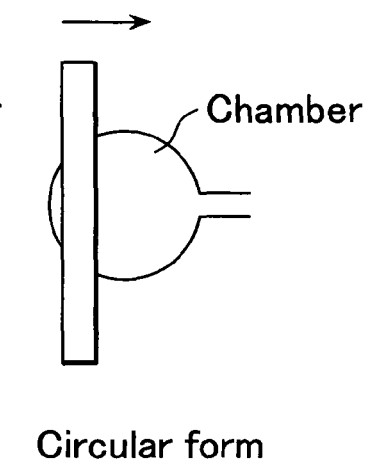

(28) Shapes of chambers may be polygons such as hexagon, rhombus, circular form or the like, as shown in FIGS. 31(a), 31(b), and 31(c).

Figure 32:
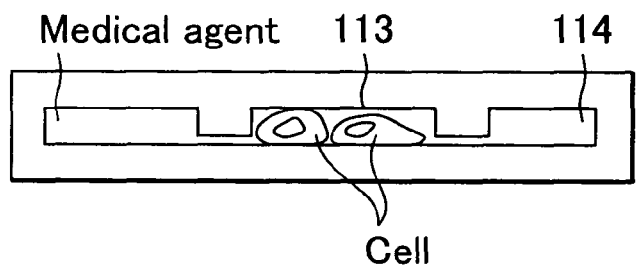
FIG. 32 illustrates a subject to be treated.

(29) A cartridge concerning the present invention can handle not only solution but also biological cells. As shown in FIG. 32, a target cell is placed in reaction chamber 113, wherein a medical agent stored in another chamber is supplied and given to the cell, thereby enabling observations of cell culture or reaction.

A cartridge concerning the present invention can also be used to synthesize proteins of cell-free systems.

Figure 33A:
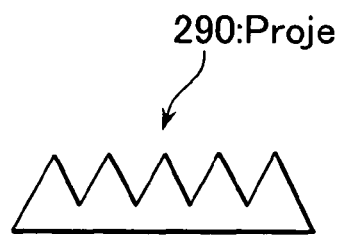
FIG. 33 illustrates an embodiment which enables cell homogenization.
Figure 33B:
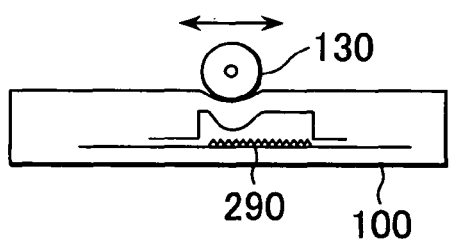

(30) Projection 290 in a triangular shape with its surface having blades as shown in FIG. 33(a) is mounted on substrate 120. Then, as shown in FIG. 33(b), roller 130 is moved from left to right and vice versa, so that cells in chamber 113 are homogenized by means of the grinding blades.

(31) The present invention has, for example, the following applications:

(a) a glucose sensor to determine the concentration of glucose in blood, wherein a cartridge is a sealed type and enables safe tests;

(b) measurements of NOx or dioxin;

(c) detection of microelements such as cadmium, cyanide arsenide and mercury in hair, water or food, wherein a cartridge is a sealed type and enables safe detection of agricultural chemicals, poisonous substances or the like using such methods as colorimetry;

(d) detection or identification of biopolymers such as DNA or RNA using a hybridization method, or detection or identification of proteins using antigen-antibody reactions;

(e) detection or identification of DNA, RNA or proteins using an electrophoresis method during detection;

(f) detection of molecules using chromatography methods such as HPLC;

(g) detection of molecules based on spectroscopy using ultraviolet light, visible light or the like;

(h) measurements of chemical reactions or changes of substances using electrochemical measurement methods, i.e., measurements to qualitatively or quantitatively detect chemical reactions such as oxidization-reduction reactions of substances or changes in conductivity ratio using electrochemical measurement methods such as the impedance method; and (i) detection or separation of cells, blood platelets or the like by identifying cells such as lymphocytes through fluorescence or the like using a flow site meter method.

Figure 34:
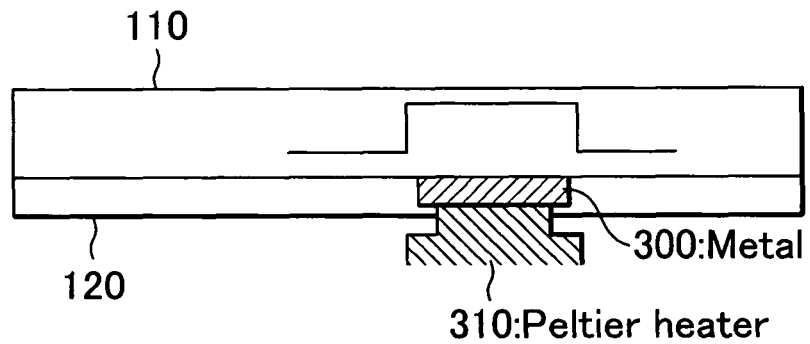
FIG. 34 is a configuration diagram of yet another embodiment of a cartridge.

(32) For amplification of PCR (Polymerase Chain Reaction) of genes, metal 300 can be embedded into substrate 120 as shown in FIG. 34, wherein increase or decrease of temperature of this metal 300 is controlled by means of Peltier heater 310, thereby facilitating heat exchange and simple PCR amplification.

Figure 35:
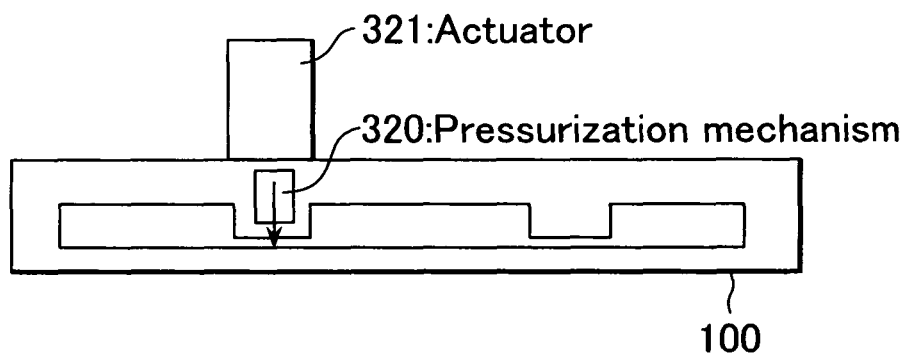
FIG. 35 is a configuration diagram of yet another embodiment of a cartridge.

(33) As shown in FIG. 35, small pressurization mechanism 320 such as a rigid body, a PZT, a shape-memory metal alloy, an actuator or the like can be buried into cartridge 100, wherein pressurization mechanism 320 is driven in conjunction with external pressure from actuator 321 or the like to apply downward pressure and to close a flow path partially.

Figure 36:
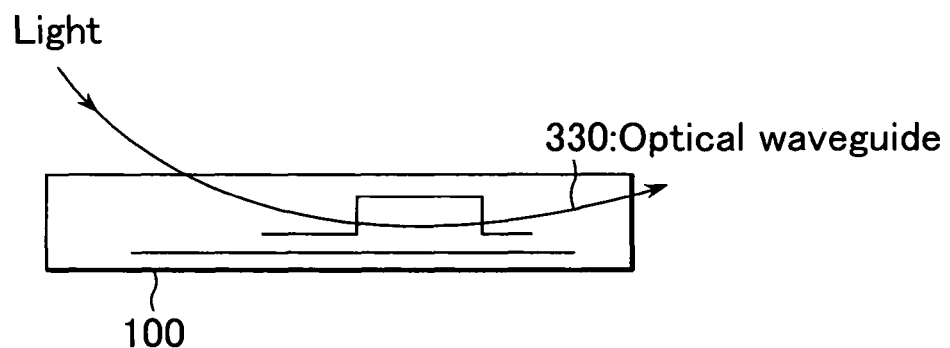
FIG. 36 is a configuration diagram of yet another embodiment of a cartridge.

(34) For using light to detect reaction substances in reaction chamber 113, optical waveguide 330 buried in cartridge 100 may be used as shown in FIG. 36.

(35) The shape of an original elastic body or substance of a cartridge can be fabricated using processing technologies such as milling, light molding, and wet or dry etching. Chambers may be fabricated by means of not only sheet adhesion as shown in FIG. 4 but also injection molding in their entirety. Molds for injection molding are fabricated using such methods as milling, light molding or etching.

Figure 37A:
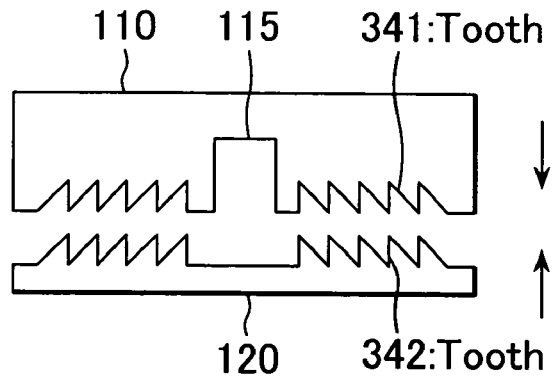
FIG. 37 illustrates an embodiment concerning a junction between an elastic body and a substrate.
Figure 37B:
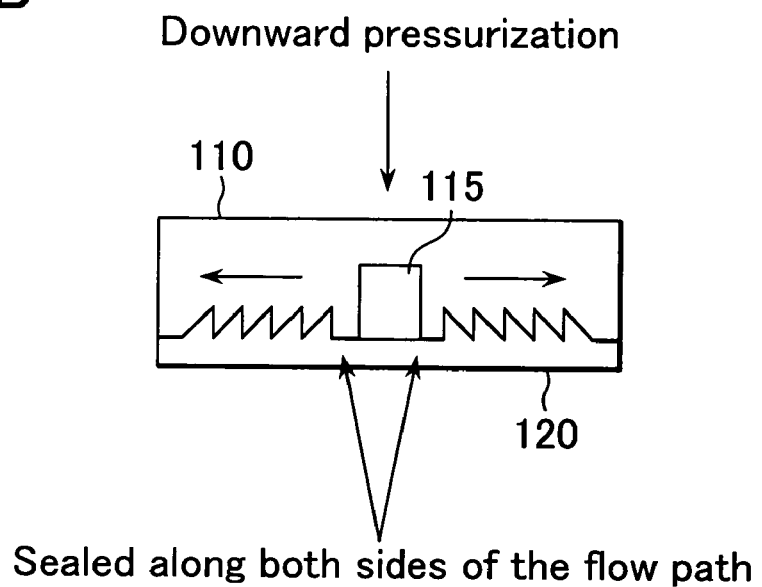

(36) Elastic body 110 and substrate 120 can be sealed not only through adhesion but also through elastic deformation or in an engagement structure. In the case of an engagement structure as shown in FIG. 37, complementary teeth 341 and 342 in a right triangular shape are formed at end faces of a joint area between elastic body 110 and substrate 120 as shown in FIG. 37(a). These teeth are engaged together as shown in FIG. 37(b). Note that these teeth are formed on entire surrounding areas of a flow path or a chamber.

Figure 37C:
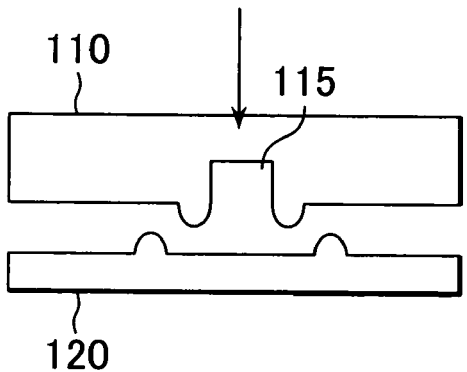
Figure 38A:
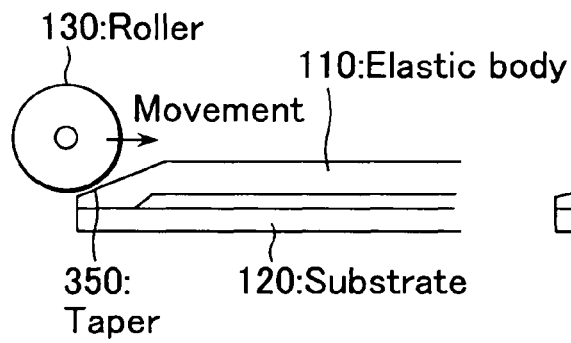
FIG. 38 is a configuration diagram of yet another embodiment of a cartridge.
Figure 38B:
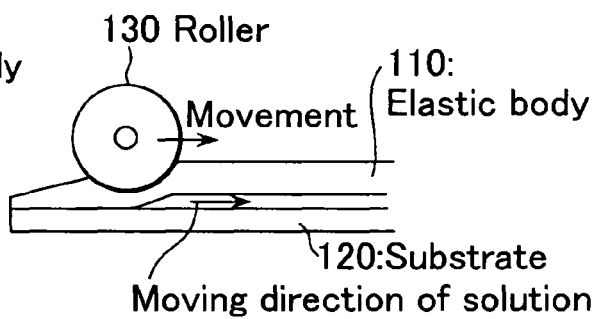
Figure 38C:
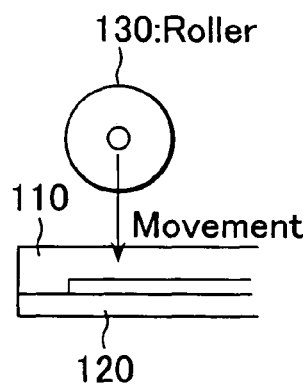
Figure 38D:
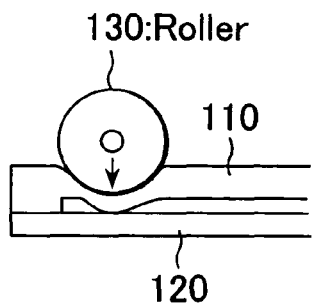
Figure 38E:
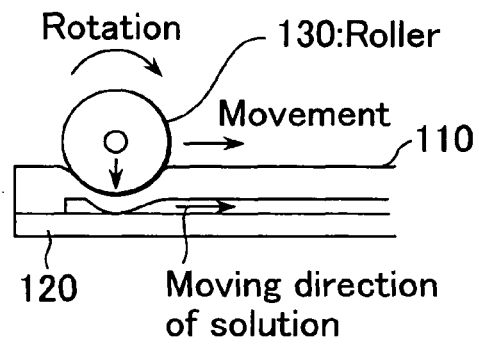

Such an engagement has a characteristic that it is difficult for elastic body 110 to expand horizontally when elastic body 110 is pressed down. If projections are provided along a chamber or a flow path as shown in FIG. 37(c), the chamber or the flow path can be sealed easily.

In addition, an external force to partially close the flow path or the chamber and to move or block fluid substance in the flow path or the chamber can be not only a mechanical force but also air pressure.

Moreover, taper 350 may be formed at a location (entrance) of a cartridge, wherein a cylindrical roller is joined first, as shown in FIG. 38. If taper 350 is provided, it is sufficient for roller 130 to move only in one direction, i.e., the right direction as shown in FIGS. 38(a) and 38(b), in order to move solution to the right direction. If a cartridge does not have a taper entrance, roller 130 needs to move in two directions, i.e., the downward direction and the right direction, as shown in FIGS. 38(c), 38(d), and 38(e).

FIG. 39 illustrates another embodiment of the present invention. FIG. 39(a) is a plan view, FIG. 39(b) is a partial cross-sectional view of chambers (A, B, C, E, and G) and convex parts (the shaded portions of FIG. 39(a)), and FIG. 39(c) is a Z-Z' cross-sectional view. For the purpose of simplification, a chamber for solution A is called chamber A, while a chamber for solution B is called chamber B (hereinafter, the same principle applies to C, E, and G).

Note that chemical reaction cartridge 100 is, as in the case of the above-mentioned embodiment, formed by elastic body 110 (such as sealed and elastic rubber) and tabular substrate 120 (which is formed by rigid materials). Materials of substrate 120 and the junction between elastic body 110 and substrate 120 are also the same as in the case of the above-mentioned embodiment.

Figure 39A:
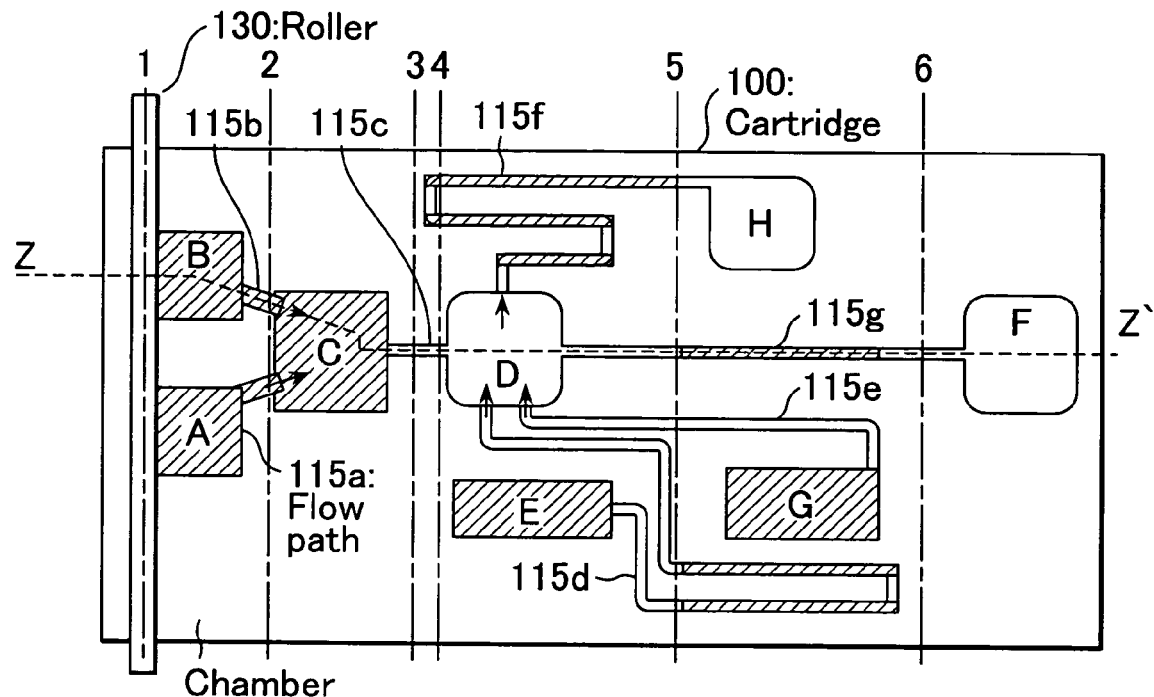
FIG. 39 is a configuration diagram of an embodiment of a chemical reaction cartridge concerning the present invention.
Figure 39B:
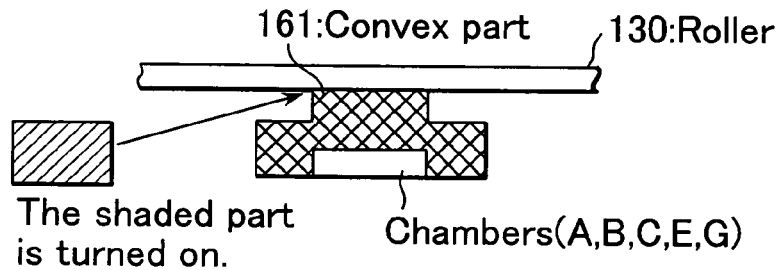

Chambers A through F for solution, each of which is concave towards the surface, are formed on the back of elastic body 110, as in FIG. 39(b). Convex part 161 is formed on the upper part of the parts of chambers (A, B, C, E, and G), which are concave towards the surface (this convex part is shaded in FIG. 39(a)).

Blood is injected into chamber A, a solution reagent for dissolving blood is injected into chamber B, and magnetic beads for capturing biopolymers such as DNA are injected into chamber C. Chamber D is a reaction chamber, wherein magnetic field is applied (not illustrated). Cleaning liquid is injected into chamber E, while buffer liquid is injected into chamber G. Chamber H is a finished product chamber to contain liquid which is reacted in reaction chamber D. Chamber F is a waste liquid reservoir.

Flow path 115 is formed for these chambers in order to link them. Chambers A and B, which are formed in an area where a convex part is formed (hereinafter called "a convex area"), are linked to chamber C, which is also formed in the convex area, through flow paths 115a and 115b. Chamber c is linked to chamber D, which is an area without a convex part (hereinafter called "a concave area"), through flow path 115c. In addition, chambers E and G, which are formed in the convex area, are linked to chamber D through flow paths 115d and 115e. Moreover, chamber H formed in the concave area is linked to chamber D through flow path 115f formed in the convex area. Chamber F formed in the concave area is linked to chamber D through flow path 115g formed in the convex area.

Figure 39C:
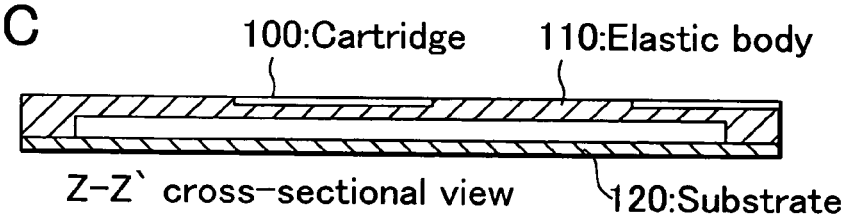

Each chamber of elastic body 110 and the flat part other than flow paths are adhered to a surface of substrate 120, as shown in FIG. 39(c), thereby allowing chambers and flow paths to be sealed by elastic body 110 and substrate 120, which in turn enables a structure wherein external leakage of solution is prevented.

Next, solution transfer operations in cartridges of the above structure are explained.

As mentioned earlier, blood, a solution reagent, cleaning liquid, and buffer liquid are pre-injected into chambers A, B, E, and G respectively which are formed in cartridge 100. Magnetic beads with surfaces to carry positive electrical charges are pre-injected into chamber C. Injections (not illustrated) are performed by means of, for example, a syringe whose needle is directly inserted into elastic body 110. Since elastic body 110 is formed by elastic materials, the needle hole self-closes if the syringe needle is withdrawn. While the needle hole is filled with an adhesive agent or the like to completely seal the hole after solution is injected, the hole can also be sealed by means of heated dissolution.

Figure 39D:
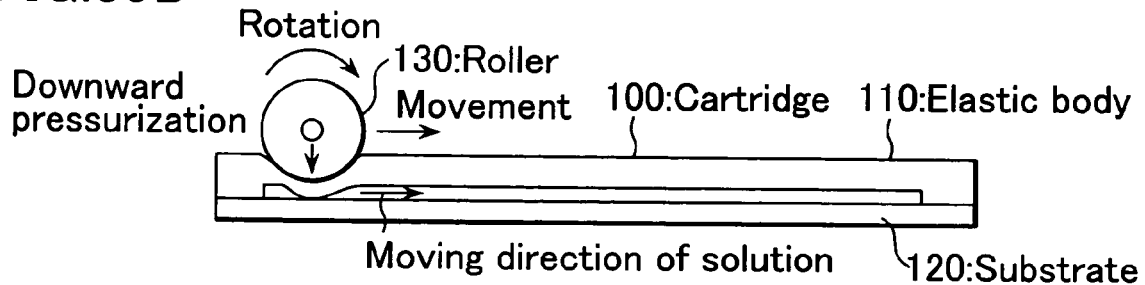

In the above configuration, as shown in FIG. 39(d), roller 130 is pressed downward from the above at the left end of cartridge 100 to the extent that the convex area is squashed, wherein blood and the reagent solution pre-injected into chambers A and B respectively are pushed out in the right direction if roller 130 is rotated and moved from position 1 to position 2 in the right direction as shown in FIG. 39(a).

As a result, the blood pre-injected into chamber A is flown through flow path 115a into chamber C wherein magnetic beads are pre-injected, while the reagent solution pre-injected into chamber B is flown through flow path 115b into chamber C, wherein the blood and the reagent solution are mixed. DNA in the blood is captured on the surfaces of the magnetic beads in chamber C.

Next, roller 130 is rotated and moved from position 2 to position 3 so that the blood, reagent solution and magnetic beads mixed in chamber C are moved through flow path 115c to chamber D. Magnetic field is applied in chamber D, wherein magnetic beads are captured.

Next, roller 130 is rotated and moved from position 3 to position 4 so that flow path 115f is squashed to block the flow into chamber H. Moreover, roller 130 is rotated and moved from position 4 to position 5. As a result, the cleaning liquid pre-injected into chamber E is flown into chamber D to clean the magnetic beads. This cleaning liquid passes through flow path 115g to flow into chamber F, wherein waste liquid is contained (flow path 115f to chamber H has been squashed and closed).

Next, roller 130 is rotated and moved from position 5 to position 6 so that buffer liquid pre-injected into chamber G is flown through flow path 115e into chamber D (a flow path to chamber F has been squashed and closed by roller 130). Then, chamber D is heated to release the DNA which has been captured by the beads. The released DNA is flown with buffer liquid through flow path 115f into chamber H to become a finished product.

Figure 40:
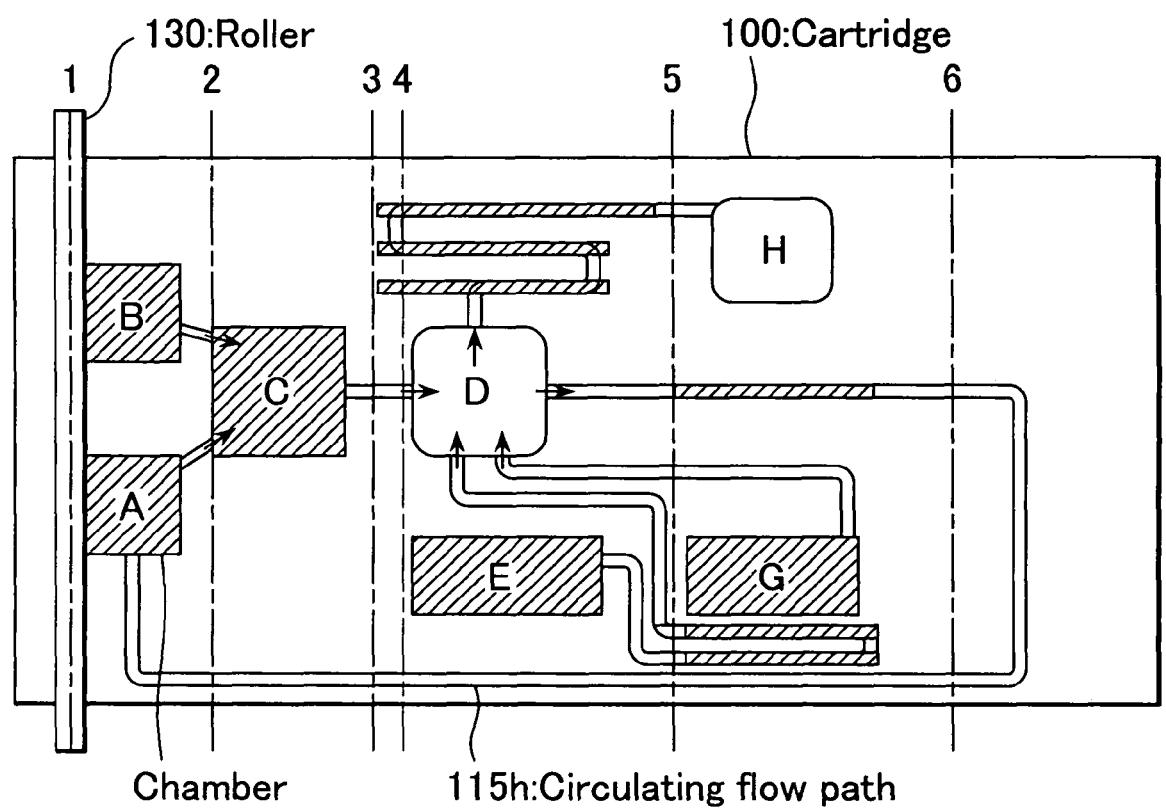
FIG. 40 is a configuration diagram of another embodiment of a chemical reaction cartridge concerning the present invention.

FIG. 40 is another embodiment of a configuration of FIG. 39. The difference from FIG. 39 is that, instead of waste liquid chamber F, circulating flow path 115*h* is formed at the drain outlet of reaction chamber D, so that waste liquid is flown back to chamber A. Movements of roller 130 and inflow and outflow operations of injectants in chambers through flow paths are the same as in FIG. 1. Such a configuration causes the internal pressure of chambers or flow paths not to increase so that liquid can be transferred smoothly. The space for waste liquid chamber F is no longer necessary, thereby enabling the cartridge for that space to be reduced.

Figure 41:
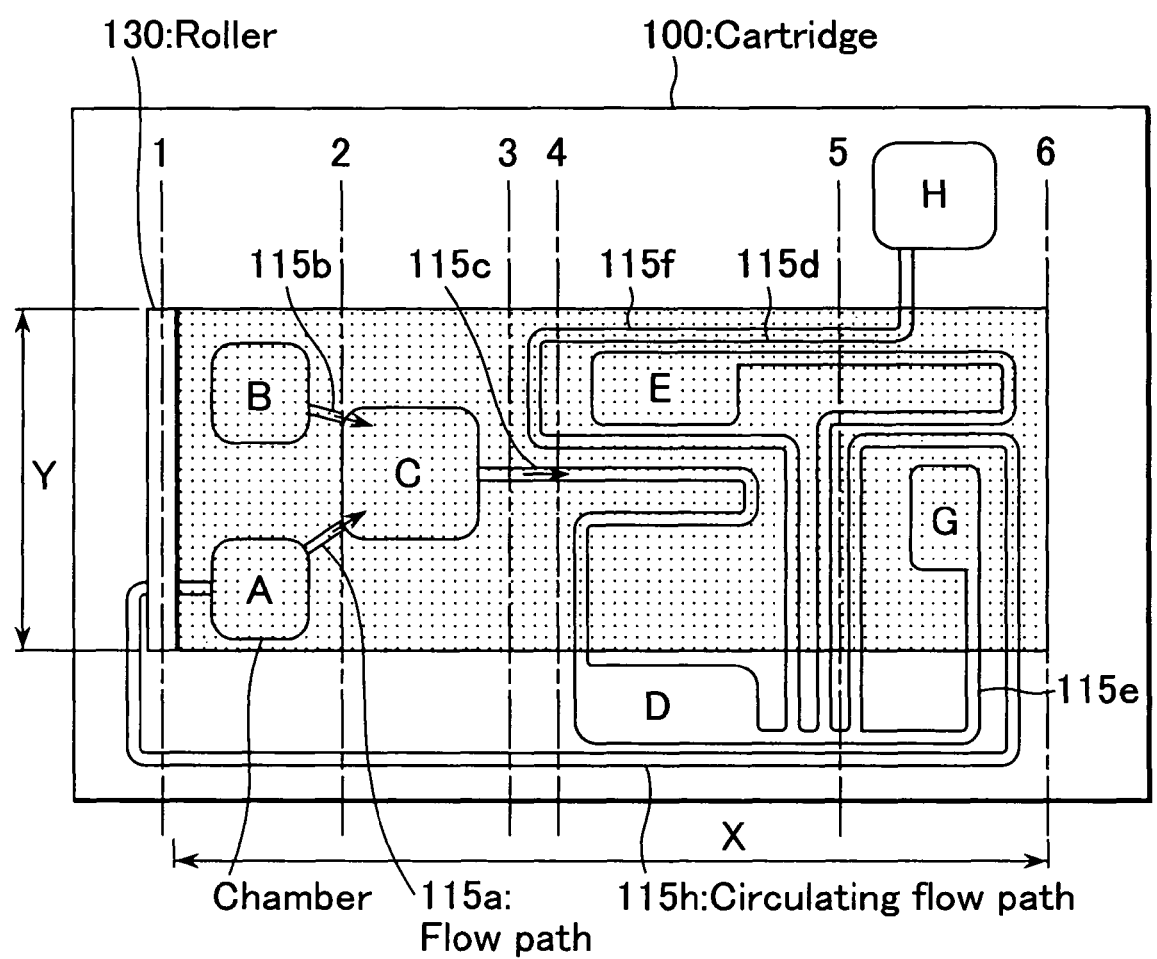
FIG. 41 is a configuration diagram of yet another embodiment of a chemical reaction cartridge concerning the present invention.

FIG. 41 illustrates an example of another embodiment, wherein a convex part as shown in FIG. 39 is not formed in a cartridge. The entire cartridge is formed in a flat shape, wherein the length of roller 130 is limited so that roller 130 moves in the X-Y range on the cartridge. Note that the same injectants as those in FIG. 39 are contained in chambers A, B, C, E, and G respectively and that chambers D and H also operate in the same way.

In the above configuration, roller 130 presses chambers A and B downward from above at the left edge of cartridge 100 to the extent that chambers A and B are squashed, wherein the blood and reagent solution pre-injected into chambers A and B respectively are pushed out in the right direction if roller 130 is rotated and moved in the right direction from position 1 to position 2 as shown in FIG. 41.

As a result, the blood pre-injected into chamber A is flown through flow path 115*a* into chamber C, while the reagent solution pre-injected into chamber B is flown through flow path 115*b* into chamber C pre-injected with magnetic beads, wherein the blood and the reagent solution are mixed.

Next, roller 130 is rotated and moved from position 2 to position 3, so that the blood and reagent solution mixed in chamber C as well as the magnetic beads which captured DNA are moved through flow path 115*c* to chamber D. Magnetic field is applied to chamber D, wherein magnetic beads are captured by the magnetic field.

Next, roller 130 is rotated and moved from position 3 to position 4, so that flow path 115*f* is squashed to block the flow into chamber H. Moreover, roller 130 is rotated and moved from position 4 to position 5. As a result, the cleaning liquid pre-injected into chamber E is flown into chamber D to clean the magnetic beads. This cleaning liquid is flown through circulating flow path 115*h* into chamber A (flow path 115*f* to chamber H has been squashed and closed).

Next, roller 130 is rotated and moved from position 5 to position 6, so that the buffer liquid pre-injected into chamber G is flown through flow path 115*e* into chamber D (a flow path to circulating path 115*e* has been squashed and closed). Then, chamber D is heated to release the DNA which has been captured by the beads. The released DNA is flown with the buffer liquid through flow path 115*f* into chamber H to become a finished product.

Figure 42:
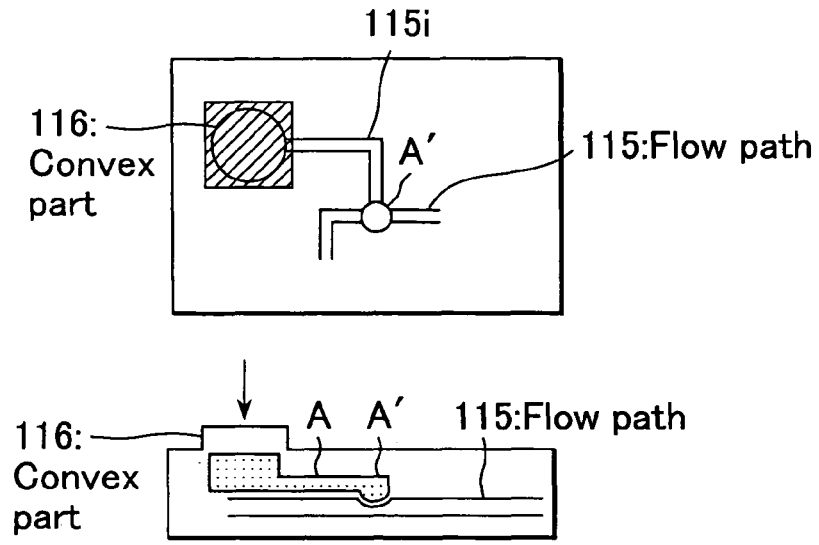
FIG. 42 illustrates yet another embodiment of a flow path pressurization method.

The downward pressurization for flow paths by means of an external force outside the cartridge is not limited to rollers. As shown in FIG. 42, oil, water, air or the like can be pre-injected for pressurization in flow path 115*i* so that convex part 161 is pressed by means of an actuator (not illustrated) and tip A' is expanded to squash flow path 115.

Figure 43:
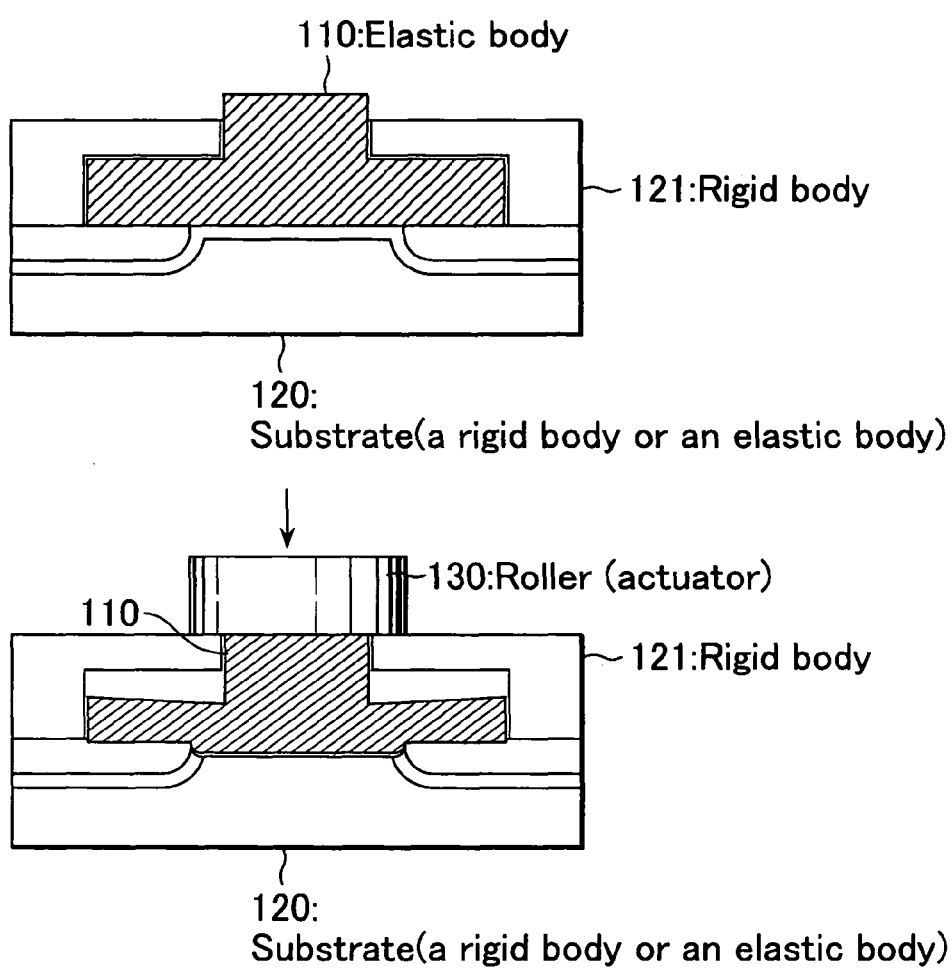
FIG. 43 illustrates yet another embodiment concerning a flow path pressurization method.

FIG. 43 illustrates another embodiment of a mechanism for pressing chambers or flow paths, wherein substrate 120 comprising chambers or flow paths, elastic body 110 with cross sections formed in a convex shape, and rigid body 121 containing elastic body 110 to project the convex part of this elastic body are combined and wherein the convex part of elastic body 110 is pressed by a roller, an actuator or the like to squash the above-mentioned flow paths or chambers. As illustrated, rigid body 121 can also act as a stopper for the actuator.

Figure 44:
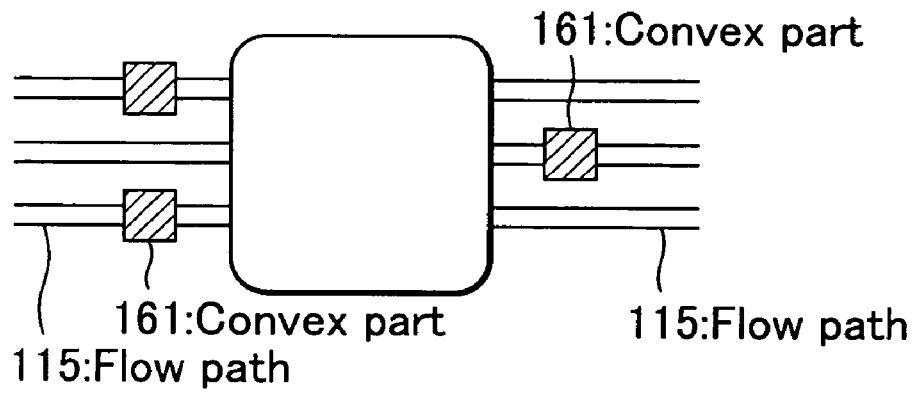
FIG. 44 illustrates an embodiment wherein six flow paths are formed for one chamber, while three open/close valves are formed.

Note that the number of flow paths 115 leading to each chamber can be arbitrary. Six flow paths are formed in FIG. 44, wherein three convex parts 161 (means of blocking flow paths) as shown in FIG. 42 or FIG. 43 are formed to become opening and closing plug valves.

Figure 45:
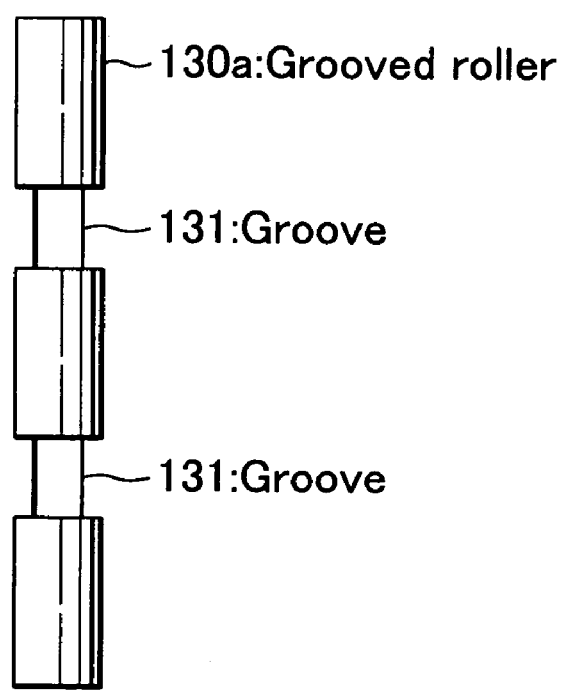
FIG. 45 illustrates another embodiment of a shape of a roller.

FIG. 45 shows grooved roller 130*a* wherein groove 131 is formed on cylindrical roller 130. Positions of convex parts or chambers formed on a cartridge can be combined in various manners.

Figure 46:
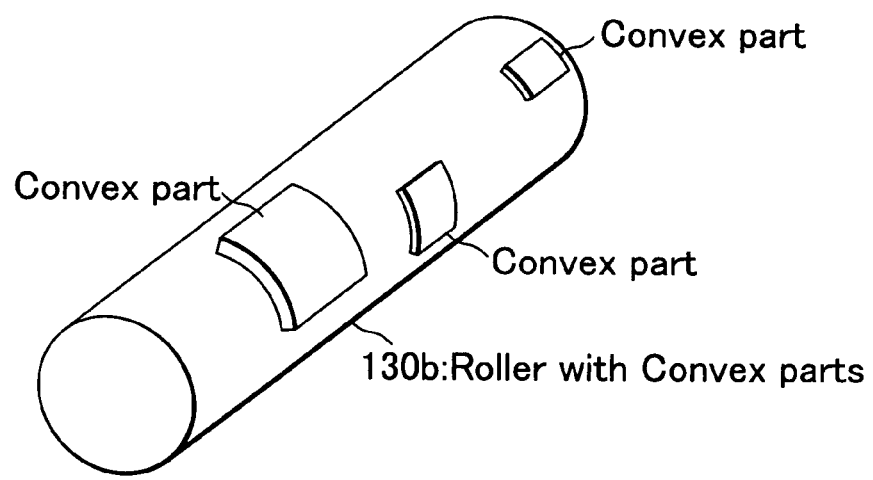
FIG. 46 illustrates yet another embodiment of a shape of a roller.

FIG. 46 shows roller 130*b* with a convex part, wherein a convex part is similarly provided to cylindrical roller 130. Even if a cartridge is flat, an external force can be applied to the cartridge partially as in the case of the convex part of FIG. 39(*b*).

Figure 47:
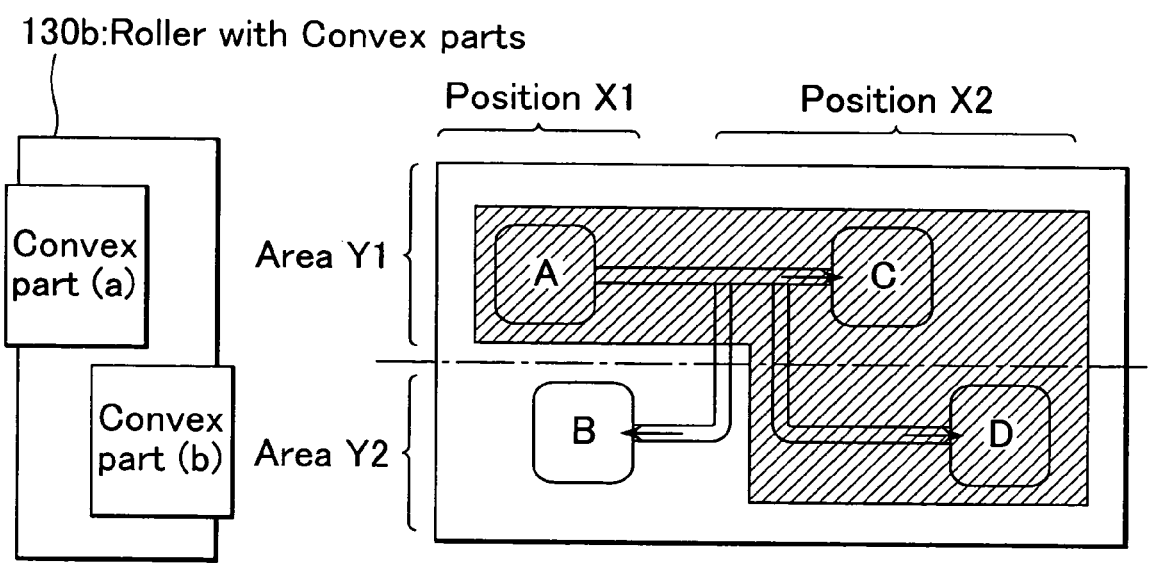
FIG. 47 illustrates an example of using a roller with convex parts.

As shown in FIG. 47, it is possible to separate the areas into Y1 and Y2 wherein the convex part (a) and the convex part (b) are used to apply pressure. In this configuration, roller 130*b* with a convex part is rotated from the left end and is moved from position X1 to position X2 to press out the liquid of chamber A located in area Y1 into chamber C and also to press the liquid back to chamber B located in area Y2.

Note that the cartridge shown in the above embodiment has the following problems under special conditions:

(1) For example, if genetic amplification is performed, heating or cooling is required. If a sample combining micro particles with DNA is used, vibration may be applied to them. However, it is difficult to transfer heat or vibration to a cartridge formed of thick materials such as tubes.

(2) If a cartridge is formed of a thin glass, a hazard is caused when solution containing viruses inside the cartridge remains when the cartridge is disposed of. In addition, cartridges of glass structure are expensive.

The embodiment shown next is capable of solving these problems. Even this chemical reaction cartridge can be heated or cooled rapidly. Sufficient vibration can be transferred to the cartridge. In addition, the influence of heating, cooling or vibration on an adjacent location is small. The cartridge is also safe and inexpensive.

Figure 48:
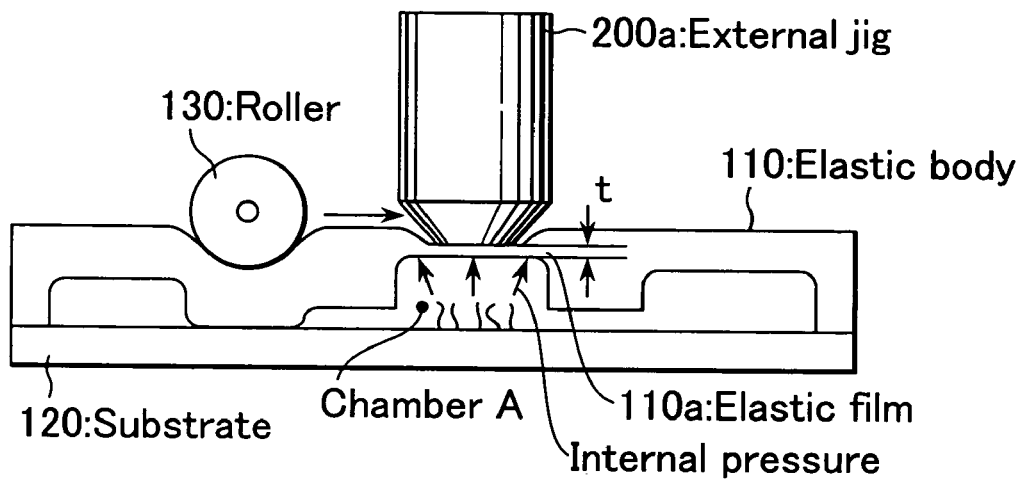
FIG. 48 illustrates a principal portion of an embodiment of a chemical reaction cartridge concerning the present invention.

FIG. 48 illustrates a principal portion of an embodiment concerning such a cartridge. This cartridge has a structure which is suitable for genetic amplification based on the PCR method or for using a sample wherein magnetic particles are combined with DNA. Note that the descriptions below deal with the characteristics only. Features other than the characteristics are the same as those of the above embodiment, and therefore, explanations of such features are omitted.

In FIG. 48, 200*a* is an action means to allow its tip to contact with thin elastic film 110*a* of the cartridge and to heat or cool a sample in chamber A (for example, reaction chamber 113 of FIG. 4(*b*)) by means of a Peltier element or the like, or to provide vibration by means of a voice coil or a piezoelement. In the following embodiment, this action means is called an external jig. Note that the sample means DNA, magnetic particles or the like as well as solution.

The forming part of elastic film 110*a* is local and is limited to the upper part of chamber A with which external jig 200*a* contacts. Elastic film 110*a* of that part is thinner than the other parts of the elastic body and is formed with a thickness of 1 mm or less. The optimum thickness "t" is, for example, 0.1 to 1 mm.

Next, operations in such a configuration are explained. A sample is injected into chamber A of the cartridge. A flow path or the like in the cartridge is blocked to raise the internal pressure of chamber A. Elastic film 110*a* remains in tension.

Note that internal pressure is not limited to a local portion of chamber A only. It can be raised across chambers and flow paths in the cartridge.

A tip of external jig 200a is pressed and adhered to the surface of elastic film 110a with raised internal pressure. Depending on treatments, the sample can be heated, cooled, or vibrated.

In a genetic amplification treatment based on the PCR method, heating and cooling are repeated. Since elastic film 110a is thin and heating and cooling are directly applied to the sample through adhered elastic film 110a, the response is far quicker than in conventional indirect heating and cooling methods.

In this manner, heating and cooling or vibration can be applied to the sample if only an elastic body on the upper part of a target chamber is formed of a thin film of 1 mm or less, to which external jig 200a is adhered. Since heating and cooling are directly applied only to the sample and rarely affect other portions with almost no transmittance, high speed response can be achieved. Also, vibration is directly applied only to the sample and rarely affects other portions with almost no transmittance.

Figure 49:
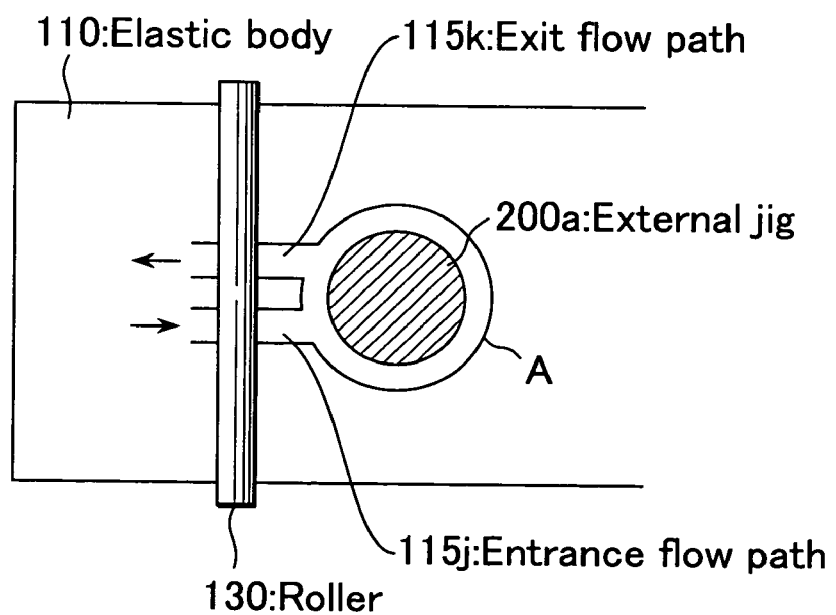
FIG. 49 illustrates a principal portion of another embodiment of the present invention.

Note that the present invention is not limited to the above embodiments. For example, as shown in FIG. 49, internal pressure of chamber A may be generated by the pressing (or introduction) of an external jig. In this case, entrance flow path 115j and exit flow path 115k, which are formed in the same direction from chamber A, are squashed simultaneously by roller 130 (to act as a plug valve) to seal chamber A, and then external jig 200a is pressed to the elastic film, thereby raising the internal pressure of chamber A.

Notch 110b may be formed in the surrounding elastic portions of an area with which external jig 200a contacts, as shown in FIG. 50(a), in order to reduce the transmittance of heat or vibration to other portions. Or, as shown in FIG. 50(b), filling member 110c made of heat insulation materials or vibration insulation materials may be buried into the notches.

Or, as shown in FIG. 51, elastic film 110a may be formed of a transparent film. If a transparent film is used, it is possible to observe fluorescent light during DNA hybridization through the window (elastic film 110a) of the transparent film by means of reading apparatus 400. If a sample is heated, laser can be emitted through the window instead of using an external jig.

Unless elastic film 110a becomes wrinkled or does not contain bubbles, the internal pressure of a chamber can almost be atmospheric pressure.

For capturing DNA, silica beads or the like can be used for magnetic beads. In this case, filters smaller than beads can be used to capture the beads themselves.

The vertical relationship between a cartridge and an external jig may be opposite to that of the embodiment. In other words, the top and the bottom of the cartridge may be reversed so that the external jig is pressed against elastic film 110a from below.

Application of pressure to an elastic body is not limited to pressurization to the entire range of the cartridge by means of a roller as shown in the above embodiments. An external force can be applied from outside the container to partially close a flow path, a chamber or both, so that fluid substance in the flow path or in the chamber will be moved or blocked.

A pump or a valve to play such a role is not limited to an external force. An external pump outside a cartridge or an internal valve made of shape-memory alloy or the like may be used.

Since cartridges of the above configurations are sealed and disposable, they have a safe structure against viruses or dangerous drugs. In addition, these cartridges are very useful from a practical point of view because they allow prescribed protocols for chemical reactions or the like to be achieved easily without differences among operators.

What is claimed is:

1. A chemical reaction cartridge for application in connection with performing chemical reactions of samples, comprising:
    a container including a rigid substrate and an elastic body adhered to a surface of the substrate, and
    a plurality of chambers connected through a plurality of flow paths are formed in the elastic body,
    wherein the elastic body is configured to be partially deformed by a roller,
    wherein in said elastic body some flow paths and some chambers are configured to be blocked by said roller, while simultaneously, other flow paths and other chambers are configured to be un-blocked,
    wherein at least two said flow paths and two said chambers are in parallel with each other with respect to a lengthwise direction of said elastic body, wherein said at least two said flow paths are spaced apart widthwise and connected at one end thereof, wherein application of external force from said roller causes simultaneous fluid flow in opposite directions in said at least two said flow paths, and
    wherein holes are provided at plural positions of the cartridge for position determination of the cartridge to determine an accurate position when said external force is applied.

2. The chemical reaction cartridge of claim 1, wherein reaction liquid, a reaction substance or a sample is injected or fixed prior to reaction in at least one of said two or more chambers.

3. The chemical reaction cartridge of claim 2, wherein an entrance is provided to inject said reaction liquid, said reaction substance or said sample so that said entrance is sealed with adhesion or fusion.

4. The chemical reaction cartridge of claim 3, wherein said entrance is provided to include said sample and wherein said entrance has a part concave from the surface of said container towards the inside so that injected said sample will not flow out of said container.

5. The chemical reaction cartridge of claim 1, wherein a target of said chemical reaction is an inorganic substance, organic substance, a biopolymer or a cell in performing treatments such as mixture, synthesis, dissolution, separation, detection or the like.

6. The chemical reaction cartridge of claim 1, wherein said force application means presses said fluid substances used in said chemical reaction out of the cartridge.

7. The chemical reaction cartridge of claim 1, wherein the surface of said elastic body is essentially flat, in a concave shape or in a convex shape.

8. The chemical reaction cartridge of claim 1, wherein said elastic body is formed of a plurality of layers, each of which has a chamber being linked through a flow path.

9. The chemical reaction cartridge of claim 1, wherein a part or a whole of said elastic body is transparent.

10. The chemical reaction cartridge of claim 1, wherein said flow path or said chamber is formed with its corners not in a right angle but in a curved shape.

11. The chemical reaction cartridge of claim 1, wherein a one-way valve with a movable portion is formed at an outlet of said flow path or said chamber, said outlet closes when a pressure is applied, or said outlet acts as a valve to expand when the pressure is applied.

12. The chemical reaction cartridge of claim 1, wherein said flow path or said chamber is formed so that it is expanded in a perpendicular direction to a length of the cartridge upon the application of the external force by said force application means.

13. The chemical reaction cartridge of claim 1, wherein the surface of said flow path or said chamber is hydrophobic or hydrophilic.

14. The chemical reaction cartridge of claim 1, wherein the surface of said flow path or said chamber is coated with fluorine-containing polymers.

15. The chemical reaction cartridge of claim 1, wherein a projection for separation and disturbance or a projection for homogenization is provided in said chamber.

16. The chemical reaction cartridge of claim 1, wherein a conductor is provided in said chamber to exchange input and output signals of a reaction substance such as voltage, electric current, heat generation or the like with external entities or wherein said chamber is formed to enable the insertion of said conductor.

17. The chemical reaction cartridge of claim 1, wherein a transparent member is formed in said chamber to allow optical detection.

18. The chemical reaction cartridge of claim 1, wherein a waste liquid reservoir is formed as one of said chambers to contain waste liquid and wherein solidification reaction agent is injected into said waste liquid reservoir to solidify waste liquid.

19. The chemical reaction cartridge of claim 1, wherein a metal is arranged in said chamber to transmit temperature changes for the purpose of performing genetic PCR amplification or a Peltier heater is arranged in said chamber to change temperature in said chamber.

20. The chemical reaction cartridge of claim 1, wherein said elastic body is a viscoelastic body or a plastic body.

21. The chemical reaction cartridge of claim 1, wherein a cartridge end to first engage with a cylindrical roller intended to move said fluid substance is formed in a taper shape.

22. The chemical reaction cartridge of claim 1, wherein, when two or more elastic bodies are combined to comprise said cartridge; a projection, a concave part or both the projection and the concave part are included in combined faces of said two or more elastic bodies to thereby join said combined faces in a sealed manner.

23. The chemical reaction cartridge of claim 1, wherein a thin elastic film is formed in a part of said elastic body to allow the contact or introduction of an action means outside said cartridge to provide heating, cooling, vibration, or light to a sample in said chamber.

24. The chemical reaction cartridge of claim 23, wherein said thin elastic film has a thickness of 1 mm or less.

25. The chemical reaction cartridge of claim 23, wherein the internal pressure of said chamber covered with said thin elastic film is equal to or greater than the pressure external to said chamber when said action means is contacted or introduced.

26. The chemical reaction cartridge of claim 23, wherein a notch has heat insulation materials or vibration insulation materials therein, and said notch is formed in an elastic portion which surrounds said thin elastic film.

27. A chemical reaction system for application in connection with performing chemical reaction of samples, comprising:
a cartridge and an external force application means;
wherein two or more chambers are provided in the cartridge for performing the chemical reaction of the samples and are linked through flow paths in a container, at least a part of which is composed of an elastic body which contains said two or more chambers,
said elastic body is configured to be partially deformed,
wherein in said elastic body some flow paths or some chambers are configured to be blocked by said force application means, while simultaneously, other flow paths and other chambers are configured to be un-blocked,
wherein at least two said flow paths and two said chambers are in parallel with other each with respect to a lengthwise direction of said elastic body, wherein said at least two said flow paths are spaced apart widthwise and connected at one end thereof, wherein application of external force from said external force application means causes simultaneous fluid flow in opposite directions in said at least two said flow paths,
wherein a first area is provided to which said external force is to be applied,
wherein a second area is provided to which said external force is not to be applied, and
wherein holes are provided at plural positions of the cartridge for position determination of the cartridge to determine an accurate position when said external force is applied.

28. The chemical reaction system of claim 27, wherein
said external force application means is a roller or an actuator, and
a contact face configured to contact said external force application means; wherein a cartridge or both of said contact face and said cartridge is formed in a convex shape in said area to which said external force is applied by said external force application means.

29. The chemical reaction system of claim 27, wherein said external force application means is a roller with a prescribed width or an actuator and wherein the width of said roller is limited to the width of an area for pressing said cartridge.

30. The chemical reaction system of claim 27, further comprising:
a substrate wherein said flow paths or said chambers are formed; and
a rigid body including said elastic body formed thereon so that a convex part of said elastic body is projected,
wherein said convex part of said elastic body is configured to be pressed to squash said flow paths or chambers and a portion of a surface of said elastic body is formed in a convex shape.

31. The chemical reaction system of claim 27, wherein flow paths for linking chambers are configured to be opened or closed due to liquid pressure or air pressure in said cartridge, which is changed by said external force application means.

32. The chemical reaction cartridge of claim 17, wherein a transparent member is buried in one of said plurality of chambers to allow optical detection.

33. The chemical reaction cartridge of claim 1, wherein said holes penetrate the cartridge.

34. The chemical reaction cartridge of claim 1, wherein said cartridge has four corners, and wherein said holes penetrate the cartridge at said four corners.

* * * * *